(12) United States Patent
Monsul et al.

(10) Patent No.: US 12,195,502 B2
(45) Date of Patent: *Jan. 14, 2025

(54) PROTEIN, AND THERAPEUTIC AND COSMETIC USES THEREOF

(71) Applicant: Quorum Innovations, LLC, Sarasota, FL (US)

(72) Inventors: Nicholas T. Monsul, Sarasota, FL (US); Eva A. Berkes, Sarasota, FL (US); Frederick T. Boehm, Sarasota, FL (US); Yu-Hsien Liao, Sarasota, FL (US)

(73) Assignee: QUORUM INNOVATIONS, LLC, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/312,484

(22) PCT Filed: May 6, 2021

(86) PCT No.: PCT/US2021/031047
§ 371 (c)(1),
(2) Date: Jun. 10, 2021

(87) PCT Pub. No.: WO2021/226318
PCT Pub. Date: Nov. 11, 2021

(65) Prior Publication Data
US 2023/0357332 A1    Nov. 9, 2023

Related U.S. Application Data

(60) Provisional application No. 63/020,860, filed on May 6, 2020.

(51) Int. Cl.
| | | |
|---|---|---|
| *C07K 14/335* | (2006.01) | |
| *A61P 31/04* | (2006.01) | |
| *C12N 15/70* | (2006.01) | |

(52) U.S. Cl.
CPC ............ *C07K 14/335* (2013.01); *A61P 31/04* (2018.01); *C12N 15/70* (2013.01)

(58) Field of Classification Search
None
See application file for complete search history.

(56) References Cited

U.S. PATENT DOCUMENTS

| | | |
|---|---|---|
| 9,416,354 B1 | 8/2016 | Liu |
| 2008/0250513 A1 | 10/2008 | Kaminski et al. |

FOREIGN PATENT DOCUMENTS

WO    2017015275 A1    1/2017

OTHER PUBLICATIONS

Hypothetical protein BKD34_08830 [Limosilactobacillus fermentum], 2 pages, provided with Sep. 20, 2021 IDS, Oct. 2016 (Year: 2016).*
Zhang et al., Journal of Ophthalmology, vol. 2015, Article ID 275435, 10 pages (Year: 2015).*
Barrera, PPAR Research, vol. 2008, Article ID 524671, 15 pages (Year: 2008).*
Kim et al., Ocul Surf. Oct. 2018 ; 16(4): 463-469 (Year: 2018).*
Chhadva et al., Ophthalmology. Nov. 2017 ; 124(11 Suppl): S20-S26 (Year: 2017).*
Otranto, Merck Manual, Eyeworms of Large Animals and of Small Animals, 2021, 7 pages (Year: 2021).*
Forsythe et al., IAAAM Archive, 1987, 6 pages (Year: 1987).*
Wang et al., J. Clin. Med., 2022, 11, 4019, 24 pages (Year: 2022).*
Yotpanya, P., et al., "Draft genome sequence of Lactobacillus fermentum 47-7, a probiotic strain isolated from healthy infants." Genbank: AOY86567.1 hypothetical protein BKD34_08830 [Limosilactobacillus fermentum].
Subhadra, B., et al., "Draft Whole-Genome Sequence of Lactobacillus Fermentum LfQi6, Derived from the Human Microbiome." Genome Announcements, 2015, 3(3): e00423-15, pp. 1-2.
Database UniProt [Online] May 26, 2009 (May 26, 2009), "SubName: Full=Uncharacterized protein {ECO:0000313IEMBL:EEI22862.1 };" retrieved from EBI accession No. UniProt:COWVN8 Database accession No. COWVN8.
Database UniProt [Online] Jan. 18, 2017 (Jan. 18, 2017), "SubName: Full=Uncharacterized protein {ECO:0000313IEMBL:AOR74302.1 };" retrieved from EBI accession No. UniProt:A0A1 D7ZWV9 Database accession No. A0A 1 D7ZWV9.

* cited by examiner

*Primary Examiner* — Melissa L Fisher
*Assistant Examiner* — Joseph Fischer
(74) *Attorney, Agent, or Firm* — SALIWANCHIK, LLOYD & EISENSCHENK

(57) ABSTRACT

The present invention provides a novel protein and biologically-active fragments and variants thereof with advantageous therapeutic and cosmetic uses. Also provided are methods of using the proteins, as well as methods of producing the proteins using a recombinant cell. Further provided are recombinant host cells transformed with a polynucleotide sequence that encodes the expression of the proteins.

4 Claims, 10 Drawing Sheets
Specification includes a Sequence Listing.

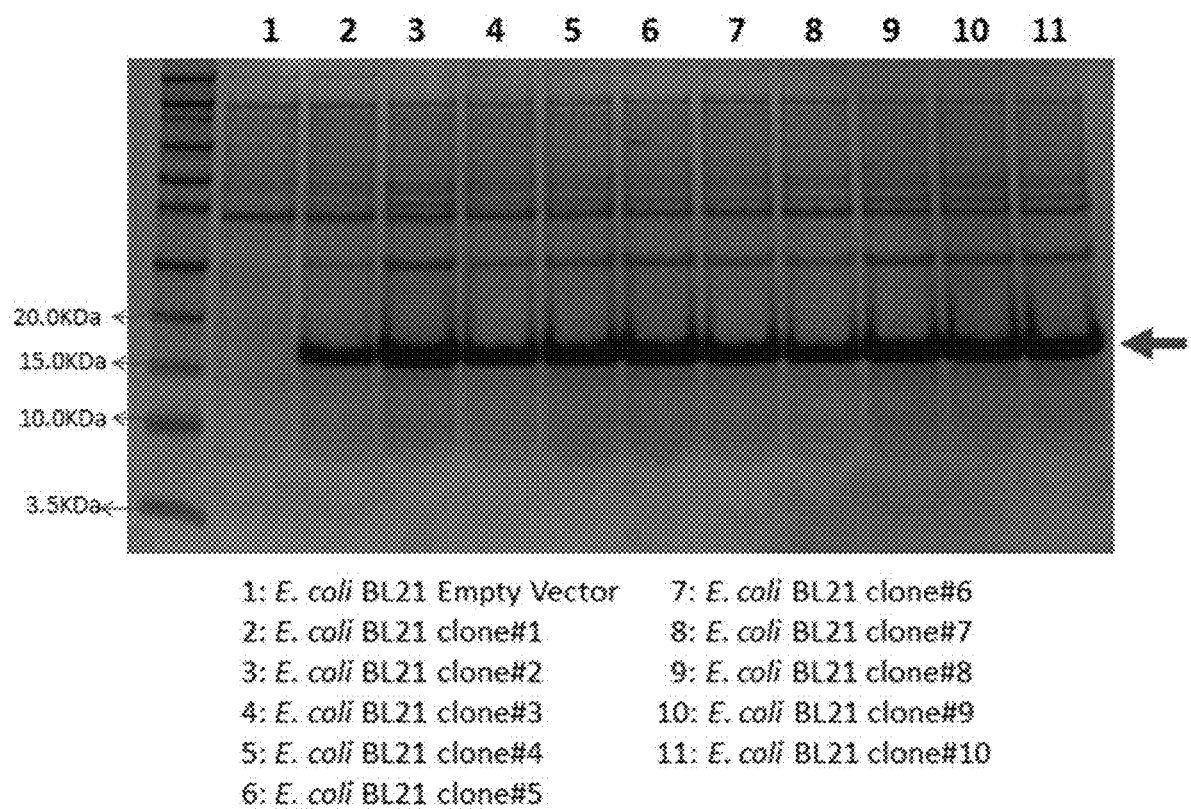
FIG. 3
Western Blot Ex Vivo Skin Test
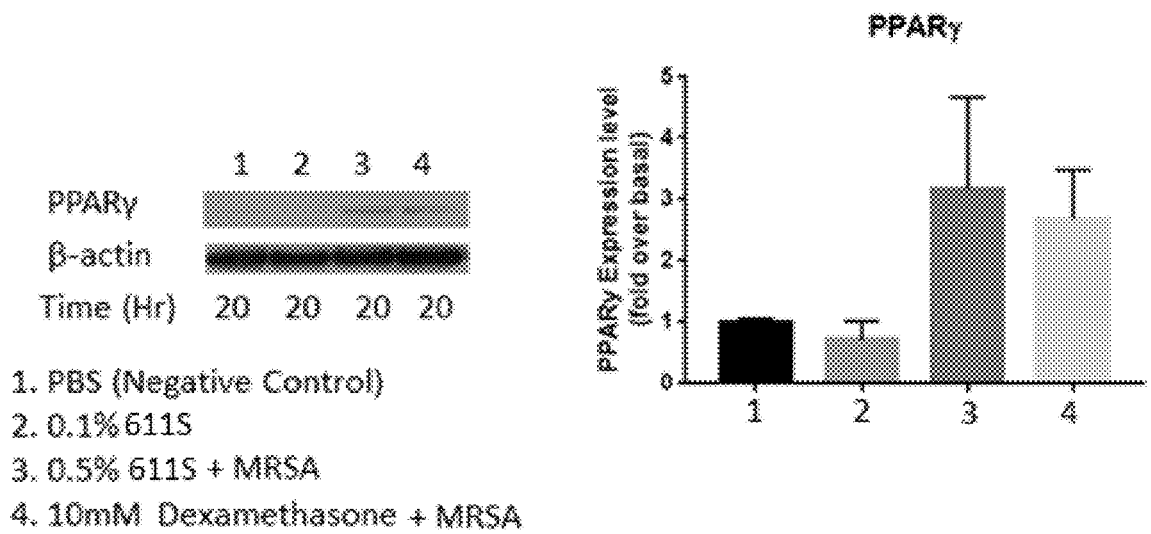
FIG. 4A
FIG. 4B

PROTEIN, AND THERAPEUTIC AND COSMETIC USES THEREOF

CROSS REFERENCE TO A RELATED APPLICATION

This application is a National Stage Application of International Application No. PCT/US2021/031047, filed May 6, 2021; which claims the benefit of U.S. Provisional Application Ser. No. 63/020,860 filed May 6, 2020, both of which are hereby incorporated by reference in their entirety.

SEQUENCE LISTING

The Sequence Listing for this application is labeled "SeqList-05May20-ST25.txt," which was created on May 5, 2020, and is 3 KB. The Sequence Listing is incorporated herein by reference in its entirety.

BACKGROUND OF THE INVENTION

Bacteria have received substantial attention for their critical roles in health and disease, both as commensals and for the production of beneficial bioactive substances.

An initial line of defense against foreign invaders, the skin is home to a diverse population of bacteria. These microbes include resident commensals, transients, and pathogens. In order to survive in the challenging environment of the skin, microbes often exhibit a biofilm phenotype, which gives competitive advantages for survival and growth. Many skin pathogens can be found living on the skin as commensals; microbial dysbiosis, host genetic variation, and immune status may drive the transition from commensal to pathogen.

Biofilms are initiated when free-floating, planktonic bacteria anchor to a biologic or inert surface such as an indwelling medical device. The attached bacteria multiply and progress from a state of monolayer to a microcolony and then to a critical mass, at which point bacterial crosstalk occurs, triggering a phenomenon known as quorum sensing that leads to the biofilm phenotype. Quorum sensing can turn on biofilm-producing genes that are not expressed in planktonic bacteria. The bacteria respond collectively to express factors that are specific to the biofilm phenotype, which leads to the secretion of an exopolysaccharide (EPS) matrix, definitive of the biofilm phenotype.

The biofilm phenotype is characterized morphologically by the formation of microbial towers, which are composed of layers of embedded, live bacteria with intervening water channels. Under the right environmental conditions, free-floating bacteria are released from the biofilms, and the cycle is continued at other surfaces.

The National Institutes of Health estimates that more than 75% of microbial infections that occur in the human body are underpinned by the formation and persistence of biofilms. Such infections include dental caries, periodontitis, musculoskeletal infections, osteomyelitis, bacterial prostatitis, endocarditis, chronic bronchitis and other states of chronic lower respiratory inflammation, cystic fibrosis pneumonia, otitis media, chronic tonsillitis, adenoiditis and device infections.

Due to different gene expression patterns, biofilm-related infections have a different clinical course and response to antibiotics than planktonic-type infections. Because antibiotics can fail to eradicate these EPS-protected microbial communities, use of antibiotics actually compounds the problem because antibiotics eliminate non-EPS-protected bacteria, facilitating replication of antibiotic-resistant bacteria. These antibiotic-resistant bacteria include methicillin-resistant *Staphylococcus aureus* (MRSA). Despite the global ramifications of MRSA, modern medicine has few treatments for pathogenic biofilm associated infections.

A MRSA infection can also cause other consequences to the infected subject. MRSA can contribute to atopic dermatitis (AD), which affects 20% of children and 5% of adults. AD presents clinically as chronically dry, pruritic eczematous dermatitis with episodic acute flares. In addition to the presence of MRSA, genetic factors contribute to AD. For example, the filaggrin protein is often deficient in AD patients.

Attacking, dissolving or otherwise weakening the bacterial biofilm matrix, interrupting the quorum mechanisms maintaining the bacterial community, and upregulating the local host innate immunity could each help to treat what would otherwise become a chronic infection or chronic biofilm-associated inflammatory disease. Penetration or dispersion of the bacterial biofilm is critical in fighting biofilm-induced chronic inflammation. Controlling pathogenic bacteria, biofilm, and metabolic products on the skin or in other organs is a major component in restoring the symbiosis of commensal skin flora and skin health. Current therapeutics, however, focus mainly on symptom-control rather than modulating the overall microbiome to inhibit the growth and reduce the adhesion and attachment of pathogenic biofilm activities.

Peroxisome proliferator-activated receptors (PPARs) are a group of nuclear receptor proteins and serve as transcription factors to regulate gene expression in response to various physiological stimuli. Their structure is highly conserved, composed of an amino-terminal activation domain (AF1), a zinc-finger DNA binding domain, a ligand-binding carboxy-terminal domain and a second activation domain at the c-terminus (AF2).

PPARα is expressed in metabolically-active tissues such as brown fat, liver, heart, muscle, kidney, and immune cells. Its ligands include docosahexanoic acid (DHA), WY 14643, clofibrate, oxidized phospholipids, phthalate esters, and various herbicides. DHA, WY 14643, and clofibrate ligands are known to increase filaggrin and heat shock protein 27 (HSP27). PPARα is a major regulator of hepatic lipid metabolism, activated under conditions of energy deprivation to initiate ketogenesis, an adaptation to prolonged fasting. PPARα synthetic ligands include the anti-hyperlipidemic fibrate drugs. Because PPARα ligands regulate hepatic lipid metabolism, they may have utility in the treatment of steatohepatitis, or fatty liver.

PPARβ/δ is expressed in metabolically active tissues including skin, intestines, liver, heart, skeletal muscle, lung, brain, thymus, spleen, keratinocytes, and various immune cells. Its ligands includes GW1514 and retinoic acid. Agonism of PPARβ/δ changes the body's fuel preference from glucose to lipids but also has been demonstrated to play a role in myelination of the corpus callosum, epidermal cell proliferation as well as differentiation, lipid accumulation, directional sensing, polarization, and migration in keratinocytes.

The gene encoding PPARγ is ubiquitously expressed, though the synthesized protein is mainly present in adipose tissue, colon and macrophages. Because its ligands include thiazolidinedione (TZD), rosiglitazone, pioglitazone, and troglitazone, PPARγ is also referred to as the "glitazone" receptor. As a regulator of adipocyte differentiation, it is important as a regulator of fatty acid storage and glucose metabolism. Compounds with activities at the PPARγ site have particularly valuable pharmacologic potential as oral, injectable or otherwise systemic treatments for diabetes, insulin resistance, metabolic syndrome, obesity, atherosclerotic heart disease and other dysmetabolic states.

PPARγ also has anti-inflammatory properties, which plays a critical role in the transition from the initial inflammatory stage of a bacterial infection to the resolution phase. In a MRSA infection, the skin in which MRSA resides becomes anoxic and glucose deprived without this transition, thus facilitating a persistent infection.

The activation or inactivation of PPARs is modulated by kinases that phosphorylate the PPAR or phosphatases that cleave the phosphate group off the PPAR. One example of a kinase that phosphorylates PPARγ is extracellular signal-regulated kinase (ERK1/2). ERK1/2 and other kinases can be induced to phosphorylate PPAR by a PPAR ligand such as ciglitazone. This phosphorylation not only affects the induction of PPAR, but it also affects the ability of ligands to bind directly to PPAR.

The glucocorticoid receptor (GR) is another nuclear receptor, acting as a transcription factor that regulates (either repressing or inducing) the expression of many genes. Many bacterial toxins modify the activation of GR, usually though inhibition of gene activation, GR translocation, or GR ligand binding.

PPAR, GR, and ERK1/2 also play roles in cancer proliferation. Ligand-mediated activation of the PPARγ receptor is also thought to contribute to the inhibition of human breast, gastric, lung, prostate, and other cancer cell lines. GR may interact with PPAR to limit the proliferation of cancer cells. In one example, GR and PPARγ may inhibit leptin gene expression, which, in turn, inhibits breast tumor growth.

Considering the substantial roles the PPAR, GR, and ERK1/2 proteins play in various signaling pathways with respect to bacterial infection, metabolism and cancer cell proliferation, novel means to influence these pathways are essential to preventing or treating bacterial infections and/or cancer, as well as modulating immune and metabolic functions.

Because much of the damage to the subject is due to the body's inflammatory response itself in cases of infection, auto-immunity and chronic inflammation, anti-inflammatory compounds are important in limiting this damage. One of the most common anti-inflammatory compounds in current use are glucocorticoid steroids (GC). These chemicals exert anti-inflammatory effects through binding and activating the glucocorticoid receptor, another nuclear transcription factor like PPAR. Their use, however, is hampered by significant adverse effects and development of glucocorticoid resistance. Therefore, a need exists to develop non-glucocorticoid GR-activators with safer side effect profiles. Because both GR and PPAR have potent immunomodulatory effects, it has been proposed that combining the use of PPAR activators with GCS would allow less GC exposure and help protect against adverse effects.

A particular need exists for the discovery of one compound which can simultaneously activate both GR and PPAR nuclear receptors without itself being a GC. A limited number of such compounds exist. These steroid-like compounds include plant terpenes such as ursolic acid (Junco J J, Cho J, Mancha A, Malik G, Wei S J, Kim D J, Liang H, DiGiovanni J, Slaga T J. Role of AMPK and PPARα in the anti-skin cancer effects of ursolic acid. Mol Carcinog. 2018 December; 57(12):1698-1706), natural fatty acids and eicosanoids, and synthetic compounds such as the PPAR ligand pioglitazone (Petta I, Dejager L, Ballegeer M, Lievens S, Tavernier J, De Bosscher K, Libert C. The Interactome of the Glucocorticoid Receptor and Its Influence on the Actions of Glucocorticoids in Combatting Inflammatory and Infectious Diseases. Microbiol Mol Biol Rev. 2016 May 11; 80(2): 495-522).

Normal placental development is critical for maternal-fetal health. There are instances when the health of the mother requires administration of medications with adverse effects to the fetus, such as GC. Excessive maternal GC administration has many potential adverse effects including fetal intrauterine growth restriction (IUGR), partially through inhibition of PPAR (Fu L, Chen Y H, Bo Q L, Song Y P, Ma L, Wang B, Xu S, Zhang C, Wang H, Xu D X. Lipopolysaccharide Downregulates 11β-Hydroxysteroid Dehydrogenase 2 Expression through Inhibiting Peroxisome Proliferator-Activated Receptor-γ in Placental Trophoblasts. J Immunol. 2019 Sep. 1; 203(5):1198-1207). Therefore, there is a particular need for non-GC GR activators with PPAR activation in maternal-fetal medicine.

SUMMARY OF THE INVENTION

The present invention provides anti-bacterial, anti-cancer, anti-inflammatory and/or metabolism modulating compositions, as well as methods for using these compositions. More specifically, the invention provides pharmaceutical, nutraceutical, and cosmetic compositions comprising a novel protein, and/or biologically-active fragments and variants thereof, and methods of using the same.

In preferred embodiments, the present invention provides novel biologically-active proteins having one or more therapeutic and/or cosmetic properties. In a specific embodiment, the present invention provides "Qi611 S," a protein having an amino acid sequence according to SEQ ID NO. 1. In certain embodiments, the present invention also provides "Qi611S Proteins," which include Qi611S, as well as biologically-active fragments and variants thereof.

In some embodiments, the Qi611 S Proteins can be characterized according to their biological activities, including, for example, antimicrobial activity, inhibition of pathogenic biofilm growth and/or adhesion, promotion of pathogenic biofilm detachment, promotion of commensal biofilm growth, enhancement of skin barrier functions and skin innate immune functions, modulation of metabolism, inhibition of inflammation, inhibition of cancer cell proliferation, and/or inducement and/or agonism of various receptors and/or kinases.

In specific embodiments, Qi611S Proteins have anti-cancer, anti-bacterial, anti-inflammatory, metabolism modulating and/or immunomodulatory activity.

In some embodiments, Qi611 S Proteins can be produced by a cell, preferably a bacterial cell. Thus, in specific embodiments, the present invention provides methods for producing a Qi611S Protein, the methods comprising cultivating a cell having a nucleotide sequence that encodes all or a portion of SEQ ID NO. 1, or a variant or fragment thereof, under conditions favorable for expression of the protein. In preferred embodiments, the nucleotide sequence is Qi611s (SEQ ID NO. 2). Optionally, the protein can be purified from the culture.

In one embodiment, the methods utilize a microorganism, e.g., *Lactobacillus fermentum* Qi6, having the Qi611s nucleotide sequence (SEQ ID NO. 2). Qi611s encodes the amino acid sequence according to SEQ ID NO. 1 (Qi611S).

In another embodiment, the cell is a microorganism that has been recombinantly altered to possess the ability to express a Qi611S Protein. In a specific embodiment, the microbe possesses all, or a portion, of the Qi611s gene.

Thus, in certain embodiments, the present invention provides a recombinant cell possessing all or a portion of the DNA sequence according to SEQ ID NO. 2, and/or that is capable of expressing a protein having an amino acid sequence according to SEQ ID NO. 1, or a fragment or variant of SEQ ID NO. 1. In an exemplary embodiment, the recombinant cell is *E. coli* BL21 or *E. coli* C43.

Such transformation of cells can be accomplished using techniques well known to those skilled in the microbiological arts. In one embodiment, the nucleotide sequence can be modified to optimize expression of a Qi611S Protein.

In preferred embodiments, the present invention provides compositions comprising a Qi611S Protein and/or a cell comprising all or a portion of a DNA sequence according to SEQ ID NO. 2, and, optionally, a pharmaceutically and/or cosmetically acceptable carrier.

Pharmaceutically and/or cosmetically acceptable carriers can comprise substances used for administrating the composition to a subject according to a specific route, including, for example, oral administration, injection (e.g., subcutaneous, intravenous, intramuscular, intraperitoneal, intrathecal, and/or subdermal), and/or topical administration (e.g., via dermal absorption). In certain embodiments, the composition can be formulated as a food item, capsule, pill, drinkable liquid, lotion, cream, emulsion, ointment, oil, gel, serum, aerosol, mist, vapor, and/or combinations thereof.

In some embodiments, the protein can be extracted and, optionally, purified from a cell culture before being formulated into the composition.

In some embodiments, the composition comprises a cell capable of producing a Qi611S Protein. In one embodiment, the cell is in a lyophilized, freeze dried, and/or lysate form. In one embodiment, the composition comprises a cell culture in a biofilm state.

In certain embodiments, the compositions of the subject invention can induce the expression of, and/or act as an agonist of, one or more molecules selected from peroxisome proliferator-activated receptors (PPARs), extracellular signal-regulated kinases (ERK 1/2), and glucocorticoid receptors (GR). Enhancement of the activity of these molecules can have downstream effects on, e.g., cancer cell proliferation, metabolism, inflammation, gene transcription, cell apoptosis, biofilm inhibition, and/or bacterial cell growth in systems such as, e.g., tumors and the insulin-growth factor (IGF) system.

Peroxisomal proliferating activating receptors (PPARs) are nuclear transcription factors present throughout the human body. There are 3 isotypes: PPARα, PPARβ and PPARγ which have important regulatory functions in many different cell types—therefore, these receptors are highly researched "druggable targets". Their activation is stimulated by ligands. For instance, PPARγ is found in fat cells, muscles, brain and immune cells. The most studied isotype, PPARγ stimulates the expression of numerous target genes and regulates glucose homeostasis, insulin sensitivity, lipid metabolism, the immune response and inflammation.

Recent findings have led to the discovery of many signaling pathways that link these nuclear receptors with human disease. PPARγ abnormalities are present in many pathophysiological conditions, including obesity, cancer, diabetes, atherosclerosis, inflammatory bowel disease and multiple sclerosis. PPARγ agonists have been studied for use as neuroprotective agents in neurologic conditions such as autism, Parkinson's, Alzheimer's, multiple sclerosis and schizophrenia.

PPARγ is the main PPAR isotype known to induce anti-inflammatory macrophage polarization. Such macrophages ("M2") are also critical for normal tissue repair, and are distinct from inflammatory macrophages ("M1") which can inhibit normal tissue healing. In many human diseases such as acute cerebrovascular accident (CVA) and acute myocardial ischemia (MI), acute M1 macrophage suppression and M2 stimulation both acutely and chronically are preferred. Therefore, PPAR-activation and PPAR-mediated M2 macrophage polarization for these disease processes is a novel and important target. Croasdell A, Duffney P F, Kim N, Lacy S H, Sime P J, Phipps R P. PPARγ and the Innate Immune System Mediate the Resolution of Inflammation. PPAR Res. 2015; 2015:549691.

Thus, in certain embodiments, the present compositions can be used for treating and/or preventing bacterial infections, metabolic dysfunction, inflammation, and/or cancer in a subject.

In certain embodiments, the compositions can modulate the expression of skin innate immune peptides and/or cytokines involved in inflammation (e.g., PPARγ, interleukin-10 (IL-10), tumor necrosis factor alpha (TNFα), PERK, toll-like receptors (TLR), and/or filaggrin). Thus, in certain embodiments, the subject compositions can be used to enhance skin innate immune functions and/or improve the health and/or appearance of skin. In specific embodiments, the composition and methods can be used for hydrating dry skin, and/or for treating a skin condition, such as atopic dermatitis.

In certain embodiments, the present invention pertains to methods of providing one or more therapeutic and/or cosmetic benefits to a subject, including, for example, controlling a bacterial infection; modulating metabolism; treating, and/or preventing the spread of, cancer; and enhancing the health and/or appearance of skin. The methods can comprise administering to the subject a composition comprising a Qi611S Protein and/or a cell capable of producing a Qi611 S Protein. In specific embodiments, the Qi611 S Protein is purified or the cell is recombinant.

The compositions can be administered to the subject via any route, including, for example, topical, oral, intravenous, intranasal, intramuscular injection and/or inhalation routes.

Advantageously, compositions and treatment methods provided herein are effective for treating and/or preventing certain cancers, metabolic dysfunctions, infections, inflammatory skin diseases, as well as improving the appearance and/or the texture of the skin and/or skin innate immune functions. Subjects treated according to the subject invention can experience, for example, relieved symptom severity and/or reduction of a bacterial infection.

BRIEF DESCRIPTION OF THE FIGURES

FIG. 3 shows a silver-stained SDS-PAGE gel used to establish the presence of Qi611S synthesized by a recombinant *E. coli* strain. The SDS-PAGE gel was loaded with samples of released protein from the recombinant *E. coli* BL21, which are identified by the bold arrow at the right of the gel. The *E. coli* strain was transformed with the Qi611s gene via the pET-15b expression vector.

FIGS. 4A-4B show the results of ex vivo skin cultures that were treated with selected concentrations of 611 S (0.1% or 0.5%) or dexamethasone (10 mM) and inoculated with MRSA. (4A) shows the amount of PPARγ present in ex vivo skin cultures and (4B) illustrates the fold changes of PPARγ present in the skin cultures. β-actin was the reference protein in the western blot used to obtain this data.

Figure 5A:
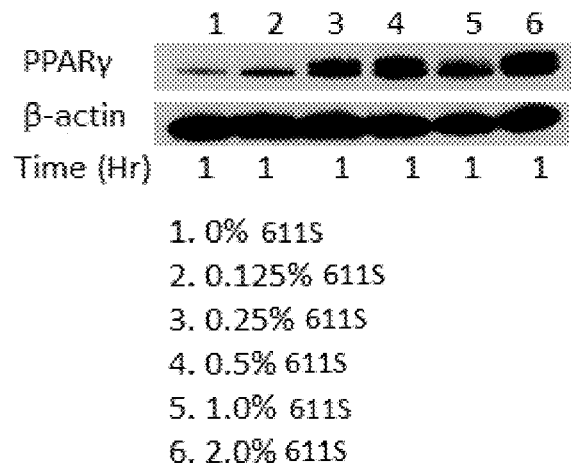
Figure 5B:
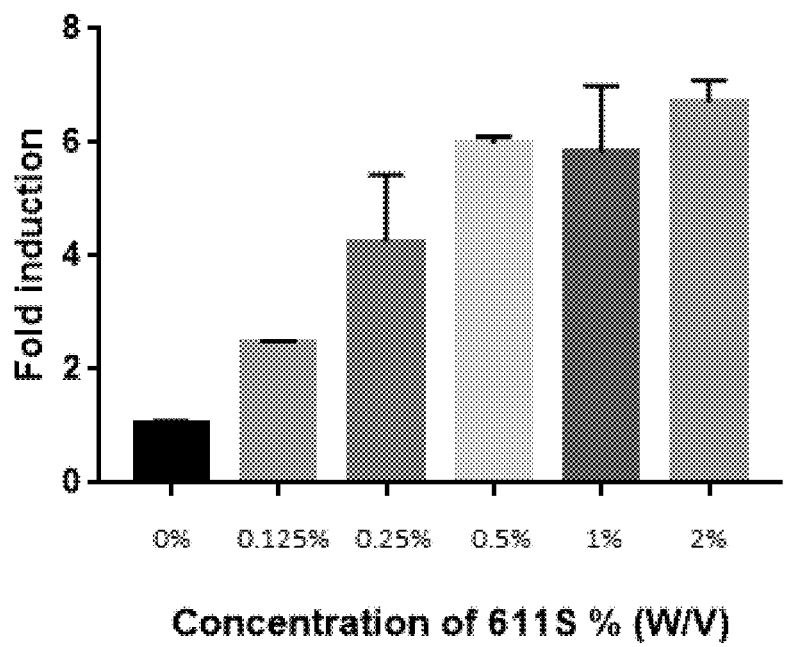

FIGS. 5A-5B show (5A) the results of a western blot measuring the amount of PPARγ present in ex vivo skin cultures that have been treated with increasing concentrations of Qi611 S (0, 0.125, 0.25, 0.5, 1.0, and 2.0%), and (5B) fold changes of PPARγ present in the ex vivo skin cultures. β-actin was the reference protein in the western blot used to obtain this data.

Figures 6A, 6B:
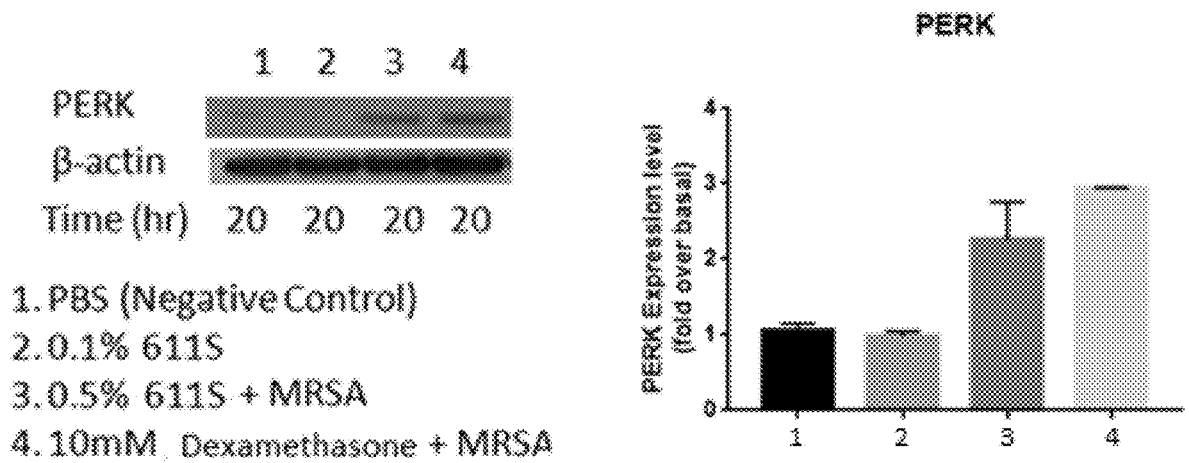

FIGS. 6A-6B illustrate (6A) the amount of pERK (phosphorylated ERK1/2) present in ex vivo skin cultures and (6B) the fold changes of pERK present in ex vivo skin cultures that were treated with selected concentrations of Qi611S (0.1% or 0.5%) or dexamethasone (10 mM) and inoculated with MRSA. β-actin was the reference protein in the western blot used to obtain this data.

Figure 7A:
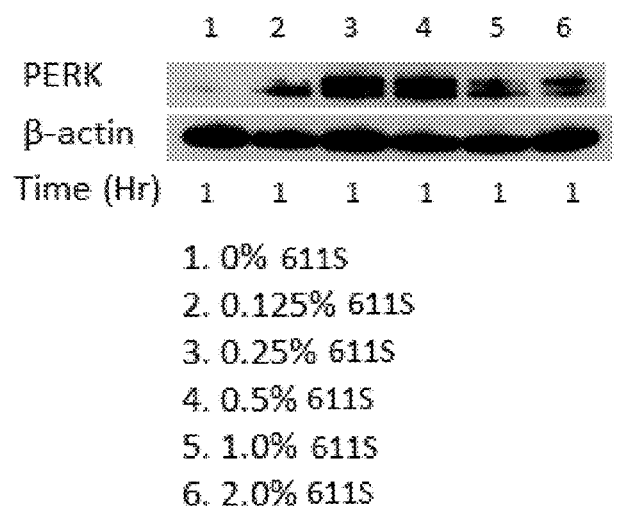
Figure 7B:
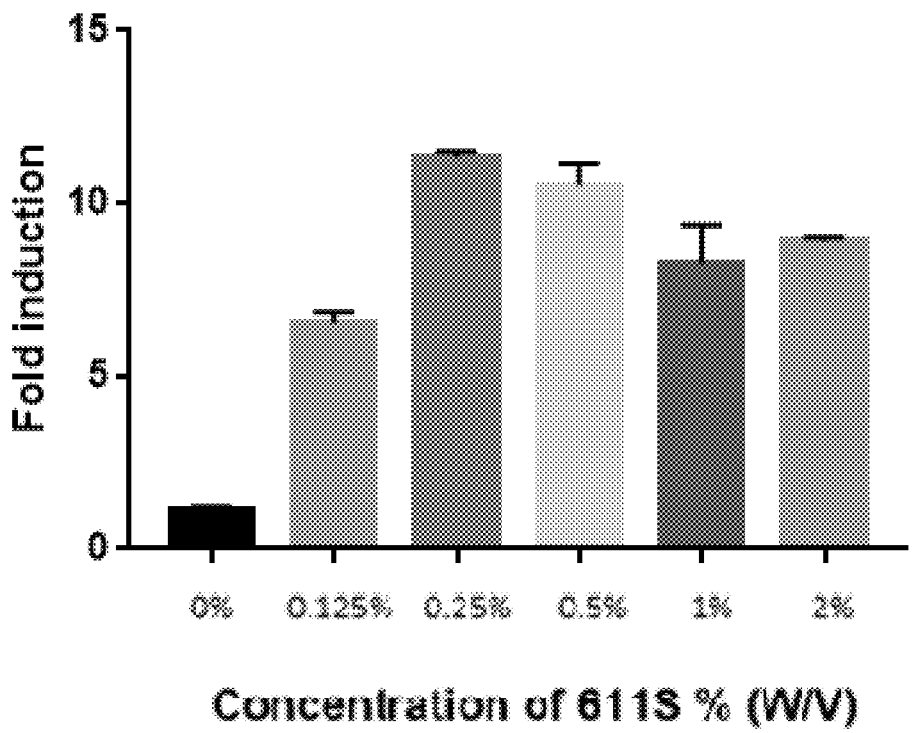

FIGS. 7A-7B show (7A) the results of a western blot measuring the amount of pERK present in ex vivo skin cultures that have been treated with increasing concentrations of Qi611S (0, 0.125, 0.25, 0.5, 1.0, and 2.0%), and (7B) fold changes of pERK present in the ex vivo skin cultures. β-actin was the reference protein in the western blot used to obtain this data.

Figure 8A:
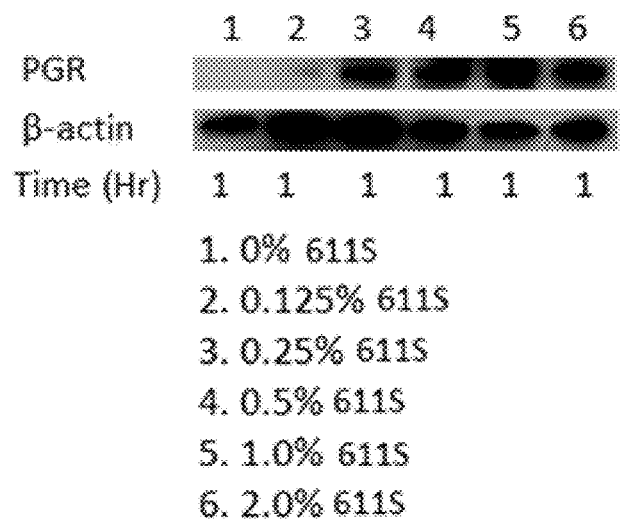
Figure 8B:
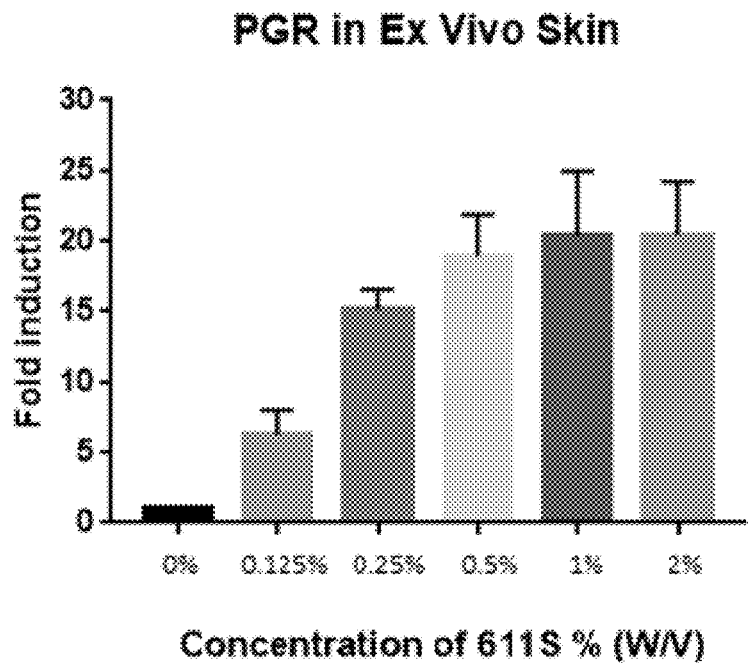

FIGS. 8A-8B show (8A) the result of a western blot measuring the amount of P-GR present in ex vivo skin cultures that have been treated with increasing concentrations of Qi611S (0, 0.125, 0.25, 0.5, 1.0, and 2.0%), and (8B) the fold changes of P-GR present in the ex vivo skin cultures. β-actin was the reference protein in the western blot used to obtain this data.

Figure 9:
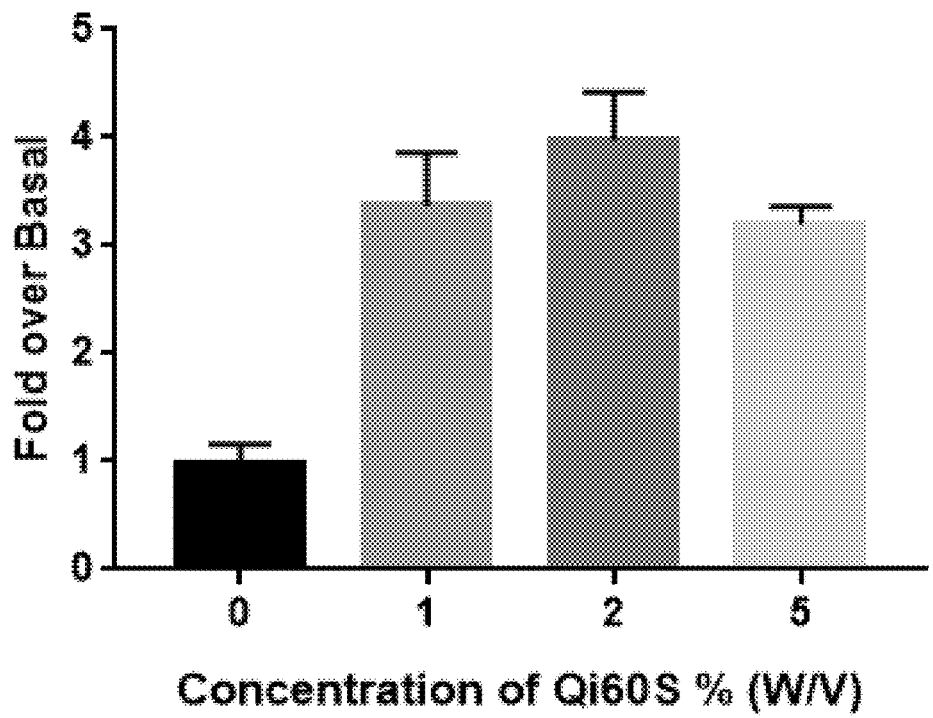

FIG. 9 shows the expression level of the gene that encodes GR in zebra fish cells when treated with increasing concentrations of Qi611S (0, 1, 2, and 5% (W/V)). This data was obtained using RT-qPCR, in which zebra fish cells were processed to isolate mRNA. The mRNA was reverse transcribed and the resulting cDNA was identified and quantified.

Figure 10A:
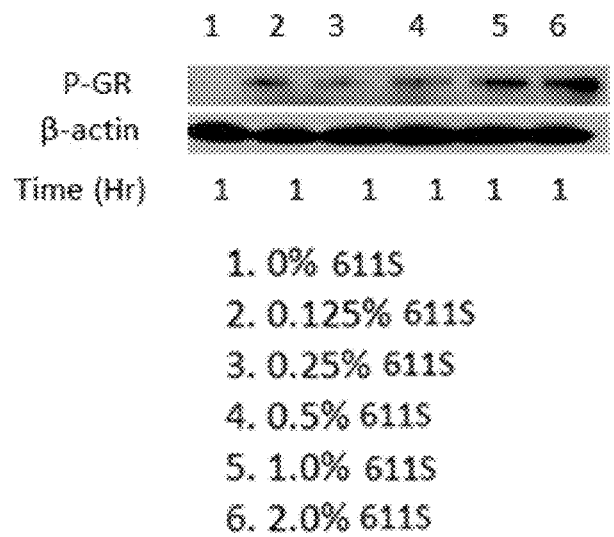
Figure 10B:
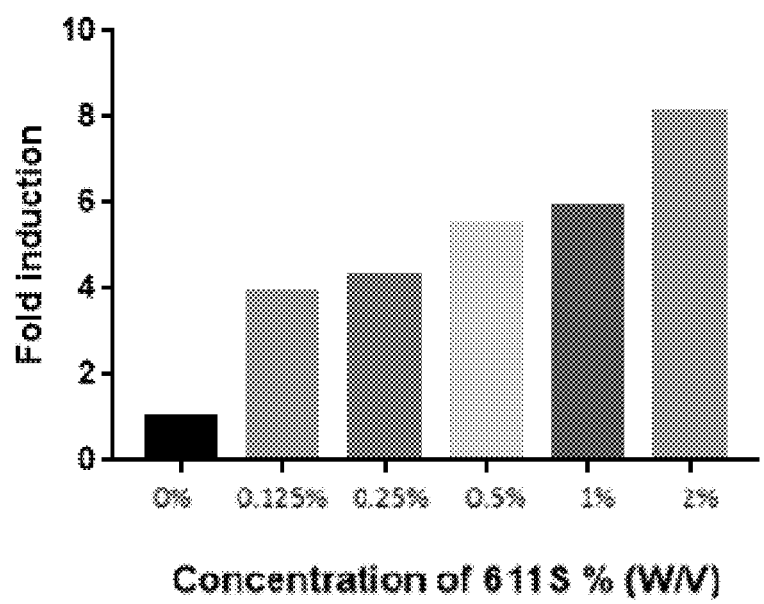

FIGS. 10A-10B show (10A) the results of a western blot measuring the amount of phosphorylated GR (P-GR) in CaCo-2 cells treated with increasing concentrations of Qi611S (0, 0.125, 0.25, 0.5, 1.0, and 2.0%), and (10B) fold changes in induction of P-GR in the treated CaCo-2 cells. β-actin was the reference protein in the western blot used to obtain this data.

Figure 11:
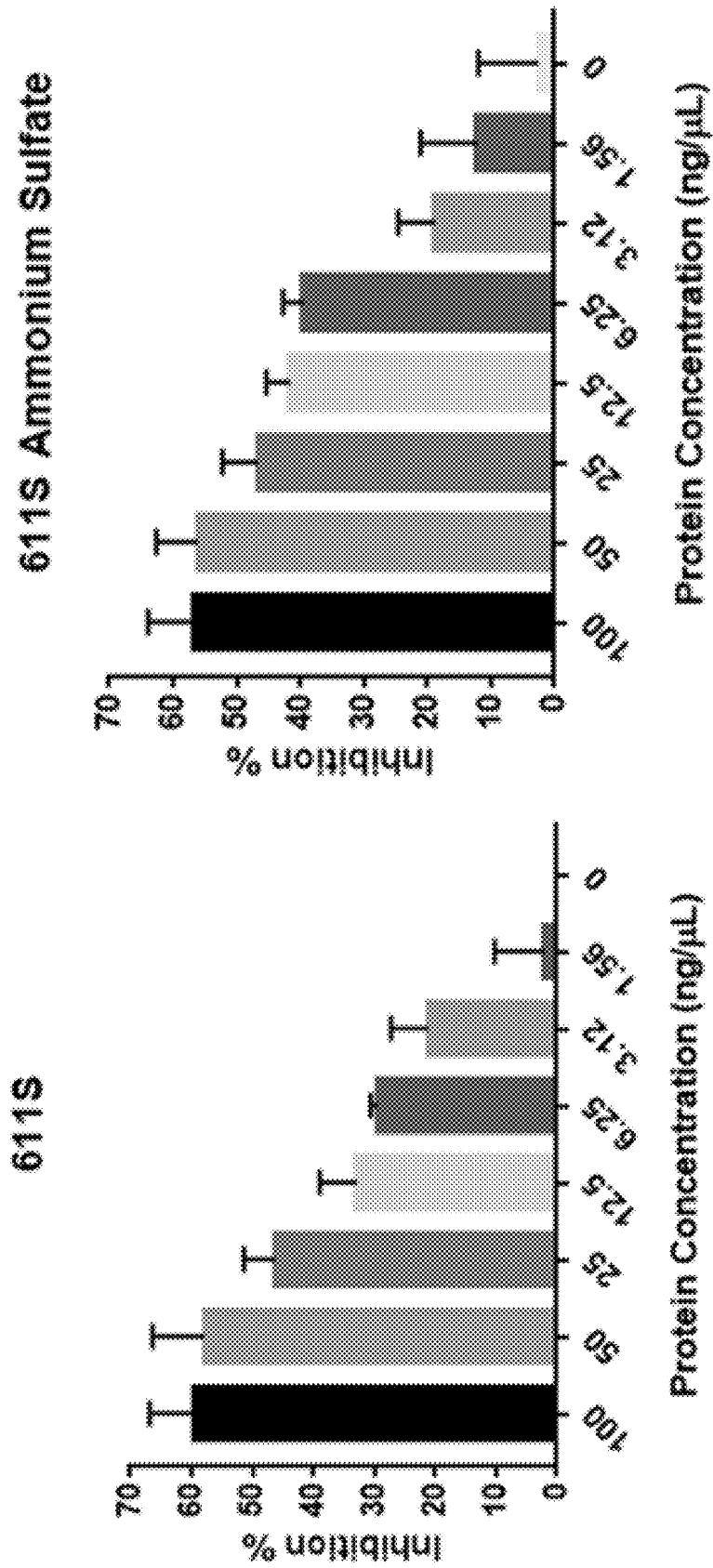

FIG. 11 shows the percent inhibition of methicillin-resistant *Staphylococcus aureus* (MRSA) biofilms using Qi611 S and ammonium sulfate precipitated Qi611 S at protein concentrations of 0, 1.56, 3.12, 6.25, 12.5, 25, 50 and 100 ng/μL.

Figure 12:
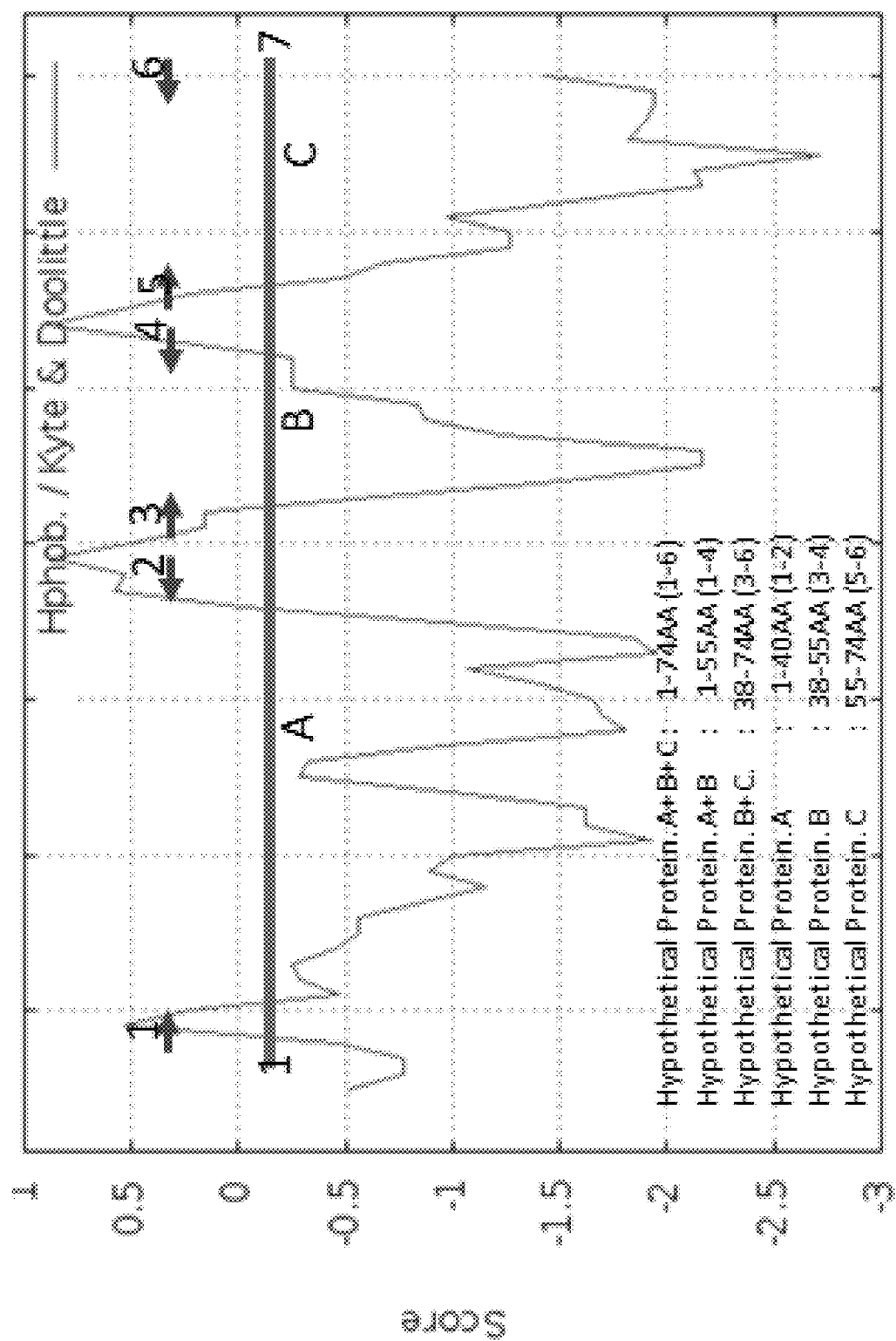

FIG. 12 is a hydrophilicity plot of Qi611 S.

BRIEF DESCRIPTION OF THE SEQUENCES

SEQ ID NO: 1 is the amino acid sequence of the protein designated as "Qi611 S." SEQ ID NO: 2 is Qi611s, a nucleotide sequence encoding the amino acid sequence of SEQ ID NO: 1.

SEQ ID NO: 3 is a forward primer, "Lacto F," useful according to the subject invention.

SEQ ID NO: 4 is a reverse primer, "Lacto R," useful according to the subject invention.

SEQ ID NO: 5 is the nucleotide sequence for the cloning/expression region of the pET-15b vector.

SEQ ID NO: 6 is an amino acid sequence for a His-tagged recombinant protein encoded by the cloning/expression region of the pET-15b vector.

DETAILED DESCRIPTION OF THE INVENTION

The present invention provides a novel protein ("Qi611S") having an amino acid sequence according to SEQ ID NO: 1, biologically-active fragments and variants thereof, as well as therapeutic and/or cosmetic compositions and methods that utilize the novel protein and/or its biologically-active fragments and variants.

Further embodiments provide cells that are capable of expressing a Qi611 S protein. In certain embodiments, the cells are recombinantly altered to possess a nucleotide sequence that encodes all or a portion of SEQ ID NO: 1. In a specific embodiment, the nucleotide sequence has SEQ ID NO: 2.

Selected Definitions

"Qi61 S" refers to a protein having the amino acid sequence of SEQ ID NO: 1. Reference to a "Qi611S Protein," in the singular or plural, refers to Qi611S, as well as biologically-active fragments and variants of 611 S.

As used herein, "gene" refers to a segment of DNA, or a nucleotide sequence, capable of expressing a polypeptide and/or amino acid chain. In certain embodiments, the gene includes regions, such as promoter regions, preceding and/or following a coding region.

As used herein, an "isolated" or "purified" compound is substantially free of other compounds, such as cellular material, with which it is associated in nature. A purified or isolated polynucleotide (ribonucleic acid (RNA) or deoxyribonucleic acid (DNA)) is free of sequences that flank it in its naturally-occurring state. A purified or isolated polypeptide is free of, for example, other cellular material with which it would be associated in nature. "Isolated" in the context of a microbial strain means that the strain is removed from the environment in which it exists in nature. Thus, the isolated strain may exist as, for example, a biologically pure culture, or as spores (or other forms of the strain) in association with a carrier.

As used here in, a "biologically pure culture" is one that has been isolated from other biologically active materials, including any materials with which it may have been associated in nature. In a preferred embodiment, the culture has been isolated from all other living cells. In further preferred embodiments, the biologically pure culture has advantageous characteristics compared to a culture of the same microbial species that may exist in nature. The advantageous characteristics can be, for example, enhanced production of one or more desirable growth by-products.

In certain embodiments, purified compounds are at least 60% by weight the compound of interest. Preferably, the preparation is at least 75%, more preferably at least 90%, and most preferably at least 99%, by weight the compound of interest. For example, a purified compound is preferably one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. Examples of metabolites include, but are not limited to, biosurfactants, biopolymers, enzymes, acids, solvents, alcohols, proteins, vitamins, minerals, microelements, and amino acids.

As used herein, "modulate" means to cause an alteration (e.g., increase or decrease).

As used herein, a "pharmaceutical," "health-promoting compound," or "health-promoting substance" refers to a compound that is useful as a medicinal and/or therapeutic drug.

As used herein, a "polypeptide," "peptide" or a "protein" refers to a polymer of amino acid residues.

As used herein, the term "subject" refers to an animal. The animal may be, for example, a human, pig, horse, goat, cat, mouse, rat, dog, ape, fish, chimpanzee, orangutan, guinea pig, hamster, cow, sheep, bird (including chicken), as well as any other vertebrate or invertebrate.

The preferred subject, in the context of this invention, is a human of any age and/or gender. In some embodiments, the subject is suffering from a health condition, disease, or disorder, while, in some embodiments, the subject is in a state of good health (e.g., free from injury or illness) but desires enhanced health and/or functioning of a particular organ, tissue, or body system.

As used herein, the terms "treating" and "treatment" refer to eradicating, reducing, ameliorating, or reversing a sign or symptom of a health condition, disease, or disorder to any extent and includes, but does not require, a complete cure of the condition, disease, or disorder. Treating can be curing, improving, or partially ameliorating a disorder. Treatment can also include improving or enhancing a condition or characteristic, for example, bringing the function of a particular system in the body to a heightened state of health or homeostasis.

As used herein, "preventing" a health condition, disease, or disorder refers to avoiding, delaying, forestalling, or minimizing the onset of a particular sign or symptom of the condition, disease, or disorder. Prevention can, but is not required to, be absolute or complete; meaning, the sign or symptom may still develop at a later time. Prevention can include reducing the severity of the onset of such a condition, disease, or disorder and/or inhibiting the progression of the condition, disease, or disorder to a more severe condition, disease, or disorder.

Ranges provided herein are understood to be shorthand for all of the values within the range. For example, a range of 1 to 20 is understood to include any number, combination of numbers, or sub-range from the group consisting of 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "recombinant" cells are modified by the introduction of a heterologous nucleic acid, or the alteration of a native nucleic acid. Thus, for example, recombinant cells can express genes that are not found within the native (non-recombinant) form of the cell or express native genes that are otherwise abnormally expressed, under-expressed or not expressed at all.

As used herein, "reduce" refers to a negative alteration, and the term "increase" refers to a positive alteration, each of at least 1%, 5%, 10%, 25%, 50%, 75%, or 100%.

As used herein, "reference" refers to a standard or control condition.

The transitional term "comprising," which is synonymous with "including," or "containing," is inclusive or open-ended and does not exclude additional elements or method steps not recited. By contrast, the transitional phrase "consisting of" excludes any element, step, or ingredient not specified in the claim. The transitional phrase, "consisting essentially of," limits the scope of a claim to the specified materials or steps "and those that do not materially affect the basic and novel characteristic(s)" of the claimed invention, e.g., the ability to preclude bacterial growth. Use of the term "comprising" contemplates embodiments "consisting" and "consisting essentially" of the recited component(s).

Unless specifically stated or is obvious from context, as used herein, the term "or" is understood to be inclusive. Unless specifically stated or is obvious from context, as used herein, the terms "a," "an," and "the" are understood to be singular or plural.

Unless specifically stated or is obvious from context, as used herein, the term "about" is understood as within a range of normal tolerance in the art, for example, within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof and from the claims. All references cited herein are hereby incorporated by reference.

Qi611S Proteins and Polynucleotide Sequences Encoding 611S Proteins

In preferred embodiments, the present invention provides a novel protein, as well as fragments and variants thereof, useful for a therapeutic and/or cosmetic purpose. In particularly preferred embodiments, the new proteins are useful for, e.g., treating bacterial, fungal or viral infections; treating, and/or preventing the spread of, cancer; inhibiting inflammation; modulating metabolism; and/or enhancing the health and/or appearance of skin. The present invention further provides nucleotide sequences that encode the novel protein, as well as fragments and variants thereof.

In certain specific embodiments, a protein of the present invention, referred to as "Qi611 S," has a molecular weight of about 8.0 kDA. "Qi611 S proteins", which include Qi611 S and biologically-active fragments and variants thereof, can be characterized according to several parameters, including biological activities, such as, for example: antimicrobial activity; inhibiting pathogenic biofilm growth and adhesion; promoting pathogenic biofilm detachment; promoting commensal biofilm growth; modulating metabolism; enhancing skin barrier functions and innate immune functions; inhibiting cancer cell proliferation; and/or inducing expression and/or activity of various receptors and/or kinases. In specific embodiments, Qi611S proteins have anti-cancer, anti-microbial (e.g., antibacterial, antifungal and/or antiviral), anti-inflammatory, metabolism modulating and/or skin immunomodulatory activity.

In certain embodiments, Qi611S Proteins can, directly or indirectly, induce expression of, and/or act as an agonist toward, one or more molecules selected from, for example, peroxisome proliferator-activated receptors (PPARs) (e.g., PPARα, PPARβ/δ, and/or PPARγ); extracellular signal-regulated kinases (ERK 1/2); and glucocorticoid receptors (GR). Whether the Qi611 S Proteins act as inducers or agonists can depend upon, for example, the biological or metabolic systems and/or the type(s) of cells (e.g., bacteria, cancer or immune cells) involved.

Modulation of PPARs, ERK and GR can have downstream effects on metabolism, inflammation, cancer cell proliferation, gene transcription, cell apoptosis, biofilm inhibition, and/or bacterial cell growth. Thus, in certain embodiments, Qi611S Proteins can be used for treating or preventing microbial infections, metabolic dysfunction, inflammation, and/or cancer by modulating one or more biological pathways involving PPAR, ERK and/or GR.

A Qi611S Protein can further be defined by its amino acid sequence. In a specific embodiment (Qi611S), the protein has the 74 amino acid sequence shown as SEQ ID NO: 1.

In certain embodiments, the proteins provided herein can also be identified based on immunoreactivity with certain antibodies, as well as other methods described below.

In certain embodiments, Qi611 S Proteins are produced by the *Lactobacillus fermentum* Qi6 bacterial strain when laboratory growth conditions are used to force the growth into a biofilm phenotype. In preferred embodiment, this bacterial strain possesses the Qi611S DNA sequence (SEQ ID NO: 2), which is capable, under biofilm phenotype conditions, of expressing a protein having SEQ ID NO: 1.

In further embodiments, a polynucleotide encoding a Qi611S Protein can be defined by, for example, the ability to hybridize with, or be amplified by, certain exemplified probes and primers (e.g., SEQ ID NOs: 3-4).

*Lactobacillus fermentum* is a Gram-positive rod. *Lactobacillus fermentum* Qi6 (Lf Qi6) can be grown in MRS media at 37° C.

A culture of the *L. fermentum* Qi6 microbe has been deposited with the American Type Culture Collection (ATCC), 10801 University Blvd., Manassas, Va. 20110-2209 USA. The deposit has been assigned accession number ATCC No. PTA-122195 by the repository and was deposited on Jun. 10, 2015.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

In some embodiments, Lf Qi6 can be grown in a biofilm phenotype. As used herein, a "biofilm" is a complex aggregate of microorganisms, such as bacteria, wherein the cells adhere to each other using a matrix usually composed of, but not limited to, polysaccharide material. The cells in biofilms have physiologically distinct properties compared to planktonic cells of the same organism, which are single cells that can float or swim in liquid or gaseous mediums, or reside on or in solid or semi-solid surfaces.

In certain embodiments, the present invention provides isolated novel polynucleotide sequences, or genes, that encode the therapeutic and/or cosmetically-useful Qi611S Proteins. Furthermore, in some embodiments, the present invention provides methods for using the polynucleotide sequences to produce recombinant hosts that express a Qi611 S Protein.

In certain embodiments, the polynucleotide sequence is Qi611S, which is 222 base pairs and encodes Qi611 S; however, in certain embodiments, different DNA sequences can encode the amino acid sequences disclosed herein because of, for example, the redundancy of the genetic code. It is well within the skill of a skilled artisan to create these alternative DNA sequences encoding the Qi611S Proteins.

As used herein, "variants" of a protein refer to sequences that have one or more amino acid substitutions, deletions, additions, or insertions. In preferred embodiments, these substitutions, deletions, additions or insertions do not materially adversely affect the therapeutic and/or cosmetic activity of Qi611 S. Variants that retain one or more biological activities of Qi611 S are within the scope of the present invention. Preferably the one or more biological activities are selected from antimicrobial activity; inhibiting pathogenic biofilm growth and adhesion; promoting pathogenic biofilm detachment; promoting commensal biofilm growth; modulating metabolism; enhancing skin barrier functions and innate immune functions; inhibiting cancer cell proliferation; and/or inducing expression and/or activity of various receptors and/or kinases.

"Fragments" of Qi611 S and its variants are also within the scope of Qi61 S Proteins, so long as the fragment retains one or more biological properties of Qi611 S. Preferably the one or more biological activities are selected from antimicrobial activity; inhibiting pathogenic biofilm growth and adhesion; promoting pathogenic biofilm detachment; promoting commensal biofilm growth; modulating metabolism; enhancing skin barrier functions and innate immune functions; inhibiting cancer cell proliferation; and/or inducing expression and/or activity of various receptors and/or kinases. Preferably, the fragment is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the full length Qi611S. The fragment may comprise, for example, one or more hydrophilic domains of Qi611 S or variant. These domains may be directly connected with intervening amino acids removed. Hydrophilic domains can be readily identified using standard procedures known in the art and as exemplified in FIG. 12.

The subject invention further contemplates fusion constructs where a Qi611 S Protein is attached, directly or indirectly (e.g., via a linker), to another moiety that may be, for example, a targeting moiety (e.g., ligand, antibody, or aptamer), a toxin, a carrier, a label, or an activity enhancer.

The subject invention further contemplates antibodies (e.g., polyclonal, monoclonal, chimeric, and humanized) to the Qi611S Proteins. These antibodies can be readily prepared by a person of ordinary skill in the art having possession of the teachings provided herein. These antibodies can be used for, for example, therapies, diagnostics, and protein purification.

In certain embodiments, a polynucleotide encoding a Qi611S Protein can be isolated, amplified and ligated into a vector. A "vector," "plasmid," or "plasmid vector" is a DNA molecule used to transfer DNA to a cell, often from one cell to another (a host cell). The vector can be replicated in the host cell; or, the vector can be a means to incorporate DNA into (or remove DNA from) a cell. A variety of means can be used to introduce a vector into a host cell. Some cells can uptake a vector without any action by one skilled in the art other than placing the vector in the cell culture. Others require chemical modification. Regardless of the means with which a cell can uptake a vector, once a host cell has the ability to do so, it is now a "competent" cell.

Figure 1:
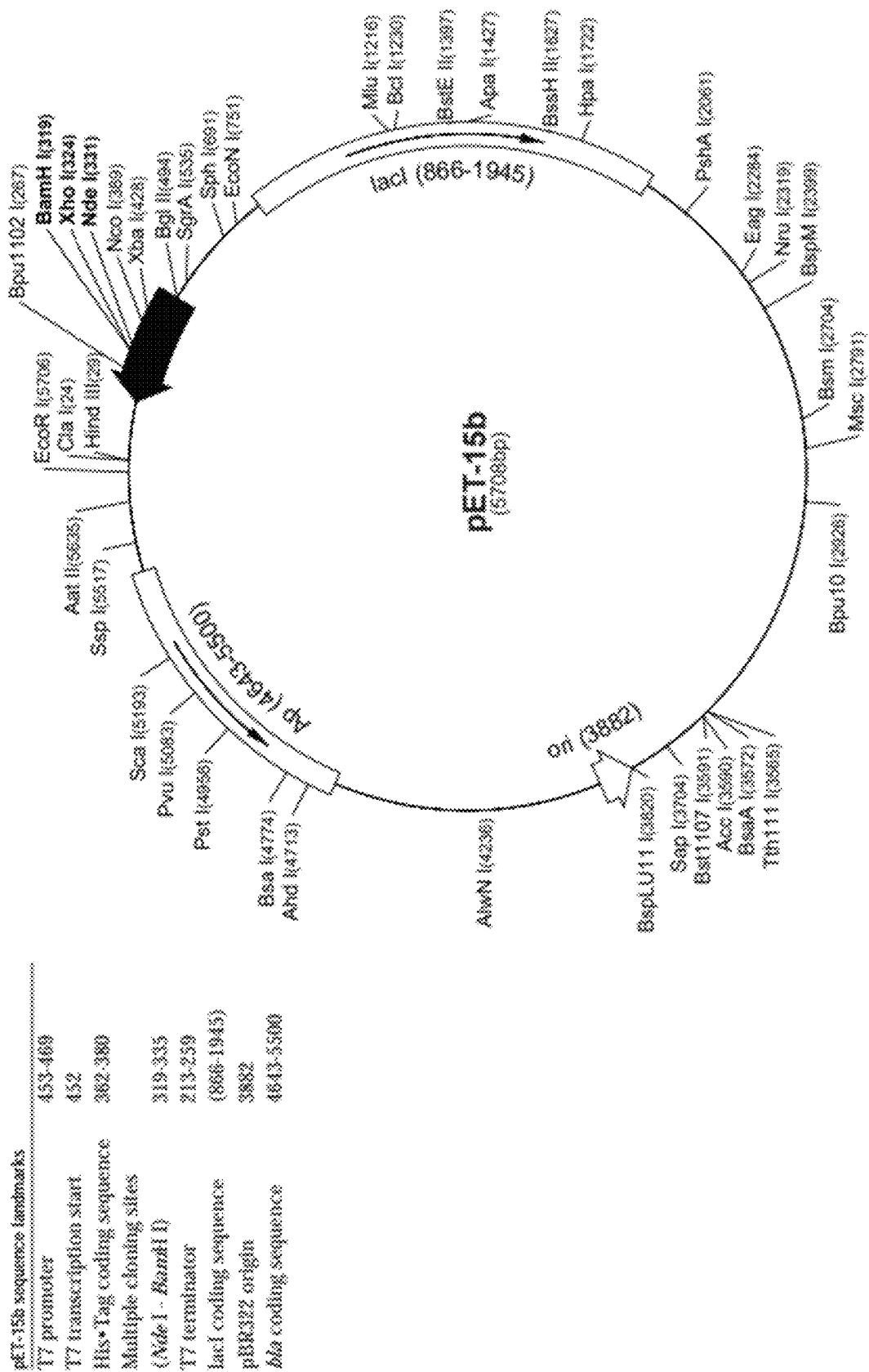
FIG. 1 shows a map of the pET-15b vector utilized according to embodiments of the present invention.
Figure 2:
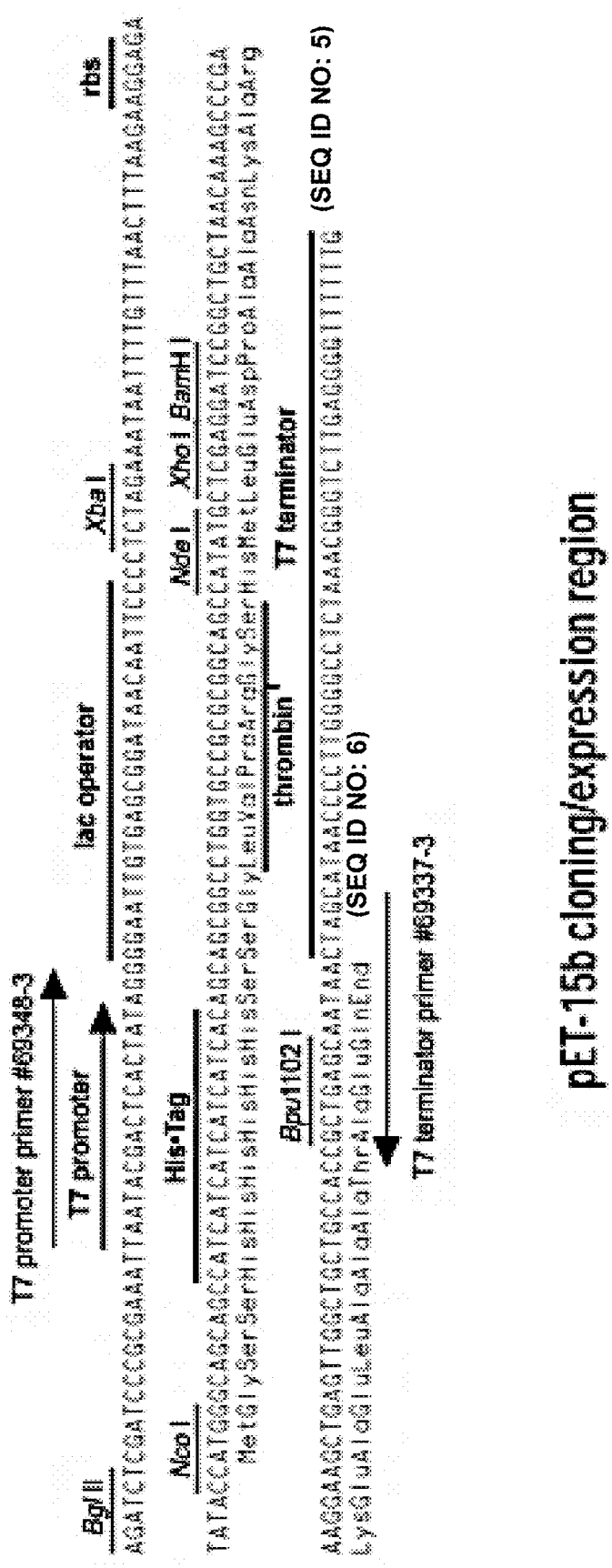
FIG. 2 shows the pET-15b cloning/expression region of the coding strand transcribed by T7 RNA polymerase.

One example of a commercially available vector is pET-15b, in which, using restriction enzyme digestion, one skilled in the art can create a vector carrying Qi611S, or other polynucleotide encoding a Qi611S Protein. The pET-15b vector carries an N-terminal His·Tag® sequence followed by a thrombin site and three cloning sites (SEQ ID NO. 6). Unique sites are shown on the circle map depicted in FIG. 1. The cloning/expression region of the coding strand transcribed by T7 RNA polymerase is shown in FIG. 2 (SEQ ID NO. 5).

In certain embodiments, the present invention pertains to the genetic transformation of host cells so as to provide these cells with the ability to produce a Qi611 S protein. For example, a vector with Qi611S (or other polynucleotide encoding a Qi611S Protein) can be transformed into a host cell (e.g., a microorganism, a plant, a fungal, and/or an animal cell) allowing for the use of recombinant cells for the production of the Qi611 S Protein.

In preferred embodiments, the host cell is a strain of *Escherichia coli*, e.g., *E. coli* BL21 or *E. coli* C43. Alternatively, the ability to transform cells, other than *E. coli*, into competent cells is well understood in the art, this includes cells chosen based on, e.g., their transformation ability, ability and efficiency for heterologous protein expression, stability of the protein in the host, presence of auxiliary genetic capabilities, lack of mammalian toxicity, ease of killing and fixing without damage to the protein, ease of cultivation and/or formulation, ease of handling, economics, storage stability and the like.

As hosts, of particular interest are prokaryotes and the lower eukaryotes, such as fungi. Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as *photobacterium, Zymomonas. Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Other possible host bacteria include, for example, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Lactobacillus jensenii, Lactobacillus Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Thermotoga martima, Geobacillus sterothermophilus* and so forth.

Bacterial hosts of particular interest include, for example, *Escherichia, Lactobacillus*, and *Bacillus*.

Eukaryotic hosts include, for example, Phycomycetes and Ascomycetes, which includes yeast, such as *Saccharomyces* and *Schizosaccharomyces*; and Basidiomycetes yeast, such as *Rhodotorula, Aureobasidium*, Sporobolomyces, and the like.

The pET-15b vector, for example, encodes a polyhistidine-tag and a thrombin cleavage site. The synthesis can be assessed through methods such as a polyhistidine-tag encoded alongside the protein to enable affinity chromatography, also referred to as affinity purification. The tag can be left attached to the Qi611S Protein synthesized by the host, or, preferably, it can be cleaved off the protein by means of the thrombin cleavage site before the recombinant protein is used.

Also within the scope of the subject instant invention are vectors or expression cassettes containing genetic constructs as set forth herein or polynucleotides encoding the polypeptides, set forth supra, operably linked to regulatory elements. The vectors and expression cassettes may further comprise selectable markers. The vectors and expression cassettes may contain additional transcriptional control sequences as well, such as, for example, strong promoters to enhance expression of cloned genes.

The expression cassette will typically include in the 5'-3' direction of transcription, a transcriptional and translational initiation region, a coding sequence of the present invention, and a transcriptional and translational termination regions. The transcriptional initiation region, the promoter, may be native or analogous, or foreign or heterologous, to the host cell. By "foreign" is intended that the transcriptional initiation region is not found in the organism into which the transcriptional initiation region is introduced.

The subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides of SEQ ID NO: 2.

The present invention also provides methods of producing a Qi611S Protein by cultivating a host cell transformed with a polynucleotide of the present invention (e.g., SEQ ID NO: 2) under conditions that allow for the expression of the polypeptide and, optionally, recovering the expressed polypeptide.

In certain embodiments, the host cell is transformed to express the polypeptide in enhanced amounts. For example, the DNA vector can include a strong transcriptional promoter sequence closely preceding the gene to be cloned. In certain embodiments, the strong promoter is a trp operon, a lac operon, a T7 promoter, and/or a pL promoter.

FIG. 3 shows a silver-stained SDS-PAGE gel used to establish the presence of Qi611S synthesized by a recombinant E. coli strain. The SDS-PAGE gel was loaded with samples of released protein from the recombinant E. coli BL21. The E. coli strain was transformed with the Qi611S gene via the pET-15b expression vector.

In certain embodiments, a Qi611S Protein can be purified from the culture in which it is synthesized through the use of tags such as polyhistidine tags and Glutathione-S-Transferase. Other means of protein purification can be used in conjunction with affinity chromatography or without affinity chromatography. Some alternative methods include centrifugation, filtration, sonication, and fractionation. The protein can be precipitated out of culture through the addition of ammonium sulfate. Also, various other chromatographic methods can be used, such as ion exchange chromatography, hydrophobic interaction chromatography, reversed phase chromatography, or immobilized metal affinity chromatography. These protein purification methods can be used in isolation or in conjunction with each other. The method or combination of methods has various advantages and disadvantages that are understood by those skilled in the art.

It will be recognized by those skilled in the art that DNA sequences of the subject invention may vary due to the degeneracy of the genetic code and codon usage. All DNA sequences that encode a Qi611S Protein are contemplated. Thus, all polynucleotide sequences that encode a Qi611S Protein are included in this invention, including DNA (optionally including an ATG preceding the coding region) that encodes SEQ ID NO: 1. The subject invention also includes polynucleotides having codons that are optimized for expression in a host cell, including any of the specific types of cells referred to herein. Various techniques for creating optimized sequences are known in the art.

Additionally, it will be recognized by those skilled in the art that allelic variations may occur in the DNA sequences that will not significantly change activity of the amino acid sequences of the peptides that the DNA sequences encode. All such variant DNA sequences are included within the scope of this invention.

The skilled artisan will understand that the exemplified sequences can be used to identify, produce, and use additional nucleotide sequences that encode Qi611S Proteins. Variant DNA sequences having at least 90%, or at least 95% identity to a recited DNA sequence and encoding a Qi611S Protein are included in the subject invention. Other numeric ranges for variant polynucleotides and amino acid sequences are provided below (e.g., 50-99%). Following the teachings herein and using knowledge and techniques well known in the art, the skilled worker will be able to make a large number of operative embodiments having variant DNA sequences without the use of undue experimentation. Specifically contemplated are homologs from other strains or species.

The fragments and the mutational, insertional, and deletional variants of the polynucleotide and amino acid sequences of the invention can be used in the same manner as the exemplified sequences so long as the fragments and variants have substantial sequence similarity with the original sequence. As used herein, substantial sequence similarity refers to the extent of nucleotide or amino acid sequence similarity that is sufficient to enable the variant or fragment sequence to function in the capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage. The identity and/or similarity can also be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

The amino acid identity/similarity and/or homology will typically be highest in critical regions of the protein that account for biological activity and/or are involved in the determination of three-dimensional configuration that ultimately is responsible for the biological activity. In this regard, certain amino acid substitutions are acceptable and can be expected if these substitutions are in regions that are not critical to activity or are conservative amino acid substitutions that do not affect the three-dimensional configuration of the molecule. For example, amino acids may be placed in the following classes: non-polar, uncharged polar, basic, and acidic. Conservative substitutions, whereby an amino acid of one class is replaced with another amino acid of the same type, fall within the scope of the subject invention so long as the substitution does not materially alter the biological activity of the compound. The following (Table 1) is a list of examples of amino acids belonging to each class.

TABLE 1

Classification of amino acids based on physical properties.

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the protein.

In some embodiments, the Qi611 S protein can have biosurfactant properties. As used herein, a biosurfactant refers to a biological surface active substance. Biosurfactants are typically amphiphiles, consisting of two parts: a polar (hydrophilic) moiety and non-polar (hydrophobic) group. Due to their amphiphilic structure, biosurfactants reduce the surface and interfacial tensions between the molecules of liquids, solids, and gases, and can act as, e.g., detergents, wetting agents, emulsifiers, foaming agents and/or dispersants.

Known examples of biosurfactants include, for example, low molecular weight glycolipids (e.g., sophorolipids, rhamnolipids, cellobiose lipids, mannosylerythritol lipids and trehalose lipids), lipopeptides (e.g., surfactin, iturin, fengycin, arthrofactin and lichenysin), flavolipids, phospholipids (e.g., cardiolipins), fatty acid ester compounds, and high molecular weight polymers such as lipoproteins, lipopolysaccharide-protein complexes, and polysaccharide-protein-fatty acid complexes.

By reducing the interfacial tension between water and oil, biosurfactants help lower the hydrostatic pressure required to move entrapped liquid to overcome the capillary effect. Biosurfactants accumulate at interfaces, thus reducing interfacial tension and leading to the formation of aggregated micellar structures in solution. The formation of micelles provides a physical mechanism to mobilize, for example, oil, pharmaceuticals, nutrients, and waste products in a moving aqueous phase, and can have powerful emulsifying and demulsifying properties. The ability of biosurfactants to form pores and destabilize biological membranes also permits their use as antibacterial, antifungal, and hemolytic agents to, for example, control pathogens, inhibit microbial adhesion to a variety of surfaces, and/or prevent the formation of biofilms. Furthermore, some biosurfactants can provide additional immune support against infections, and enhance the bioavailability of other active components.

Advantageously, the biosurfactants according to the present invention are capable of one or more of the following: killing pathogenic agents in/on the skin, modulating the skin's immune system, killing melanocytes to allow for replacement cells to grow, reducing oxidative stress, enhancing multiplication and function of keratinocytes and fibroblasts, and contain components that enhance dermal penetration of the composition. Thus, they provide therapeutic benefits themselves, and can also enhance the effectiveness of other components that may be present in the topical composition in treating skin conditions related to wounds, such as burns, and/or scarring, as well as rejuvenating aging and/or damaged skin.

Therapeutic and Cosmetic Uses for Qi611S Proteins

The Qi611S Proteins of the present invention can be useful for a variety of therapeutic and/or cosmetic applications. For example, in certain embodiments, the present invention provides compositions and methods for treating cancer, microbial infections, metabolic dysfunction, inflammation, as well as for enhancing the health and/or appearance of skin.

"Therapeutic," as used herein, means useful for treating and/or preventing a disease, condition or disorder. "Cosmetic," on the other hand, means restoration and/or improvement of a subject's appearance. For example, a cosmetic composition may enhance the hydration level of the skin. Increased hydration level is known to improve the appearance of the skin and lead to a healthier, more youthful cosmetic appearance.

In preferred embodiments, the invention provides pharmaceutical and/or cosmetic compositions comprising a Qi611S Protein (e.g., SEQ ID NO: 1) and/or a cell capable of producing a Qi611S Protein, as well as methods of using the same. In certain embodiments, the compositions can optionally comprise a pharmaceutically- and/or cosmetically-acceptable carrier.

In further embodiments, the invention provides methods of providing a therapeutic and/or a cosmetic benefit to a subject in need therein, wherein a composition according to the present invention is administered to the subject. In some embodiments, a therapeutically- or cosmetically-effective dose of the composition may be administered to the subject, e.g., one, two, three, or more times daily, for as long as needed, or until the desired benefit is achieved.

As used herein, a "therapeutically-effective" amount or dose is an amount or dose of a compound or composition that, when administered to a subject, is capable of treating or improving a condition, disease, or disorder in a subject or that is capable of providing enhancement in health or function to an organ, tissue, or body system.

The actual amount will vary depending on a number of factors including, but not limited to, the particular condition, disease, or disorder being treated or improved; the severity of the condition; the particular organ, tissue, or body system of which enhancement in health or function is desired; the weight, height, age, and health status of the patient; and the route of administration. Prescription of treatment, e.g., decisions on dosage etc., is within the purview of general practitioners and other medical doctors, and typically takes into account the disorder to be treated, the condition of the individual patient, the site of delivery, the method of administration and other factors known to practitioners.

As used herein, a "cosmetically-effective" amount or dose is an amount or dose of a compound or composition that, when administered to a subject, is capable of providing a cosmetic benefit to the subject.

In certain embodiments, the therapeutic and/or cosmetic benefit is treatment and/or prevention of a disease, disorder or condition, such as, for example, skin innate immune dysfunctions, bacterial infections, metabolic dysfunction, inflammation and/or cancer. In certain embodiments, the therapeutic and/or cosmetic benefit is improvement of the appearance and/or texture of skin.

In some embodiments, the compositions and methods utilize a biologically pure culture of a cell capable of producing a Qi611 S Protein. The cell can be a microorganism that possesses SEQ ID NO: 2, such as, for example, *L. fermentum* Qi6; and/or the cell can be a recombinant cell engineered to have a polynucleotide sequence that encodes a Qi611S Protein, e.g., SEQ ID NO: 2. In an exemplary embodiment, the recombinant cell is *E. coli* BL21 or *E. coli* C43.

In certain embodiments, the cell is a bacterial strain capable of growing in both planktonic and biofilm phenotypes. In one embodiment, the cell is in a lyophilized, freeze dried, and/or lysate form.

In one embodiment, the protein can be extracted and, optionally, purified from a cell culture before use in the present compositions and methods. As used herein, the term "extracting" refers to processing a cell culture to obtain one or more desired compounds. The processing may involve, for example, filtering, centrifugation, sonication, pressure treatment, radiation treatment, lysing, treatment with solvents or other chemicals, and combinations of these treatments. The resulting extract can be in the form of, for example, a supernatant such as that produced via centrifugation. The extract can also include cell mass obtained through centrifugation. The cells may be intact or not intact, viable or not viable. The extract may comprise cell membrane components and/or intracellular components. In certain embodiments, the extract is at least 80, 85, 90, or 95%, by weight, cell mass. In certain other embodiments, the extract is at least 80, 85, 90 or 95%, by weight, protein.

The compositions provided herein may contain a single (unit) dose of cells, or lysate, or protein extracted therefrom. In some embodiments, a composition according to the present invention may comprise a dose of at least about 0.01% to about 100%, by weight, of a Qi611S protein, or at least about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0%, about 55%, about 60%, about 65%, about 70%, about 75%, about 80%, about 85%, about 90%, about 95%, or about 99% by weight of a Qi611S protein.

In some embodiments, the compositions may comprise a dose of at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, by weight of the Qi611 S protein.

Suitable doses of bacteria (intact, lysed or extracted) may be in the range $10^4$ to $10^2$ CFU, e.g., one of $10^4$ to $10^{10}$, $10^5$ to $10^8$, $10^6$ to $10^{12}$, $10^6$ to $10^{10}$, or $10^6$ to $10^8$ CFU. For the purpose of the present invention the abbreviation CFU shall designate a "colony forming unit" that is defined as the number of bacterial cells as revealed by microbiological counts on agar plates.

In certain embodiments, the Qi611S Protein and/or cells comprising a nucleotide sequence encoding a Qi611S Protein can, directly or indirectly, induce the expression and/or act as an agonist of one or more molecules selected from, for example, peroxisome proliferator-activated receptors (PPARs), namely, PPARα, PPARβ/δ, and/or PPARγ, extracellular signal-regulated kinases (ERK 1/2), and glucocorticoid receptors (GR).

In some embodiments, the Qi611 S Protein and/or cells comprising a nucleotide sequence encoding a Qi611S Protein can, directly or indirectly, inhibit action of PPARs, ERK and/or GR.

Modulation of PPARs, ERK and GR can have downstream effects on, for example, cancer cell proliferation, gene transcription, cell apoptosis, biofilm inhibition, metabolism modulation, inflammation, and bacterial cell growth. Thus, in certain embodiments, the present compositions can be used for treating or preventing bacterial infections, metabolic dysfunction, inflammation and/or cancer.

"Inducing," as used herein, can include increasing or enhancing expression of a gene that encodes, for example, a receptor protein or kinase of interest, and/or otherwise increasing or enhancing the activity of the receptor protein or kinase in a particular system via, for example, ligation, phosphorylation, de-phosphorylation, and/or structural modification. In an exemplary embodiment, Qi611 S can induce PPARG, the gene that encodes PPARγ expression in humans.

An "agonist" is a substance that typically causes an action after it binds to a receptor. Often the receptor is a protein. Single agonists can lead to cascades of signals, in which the initial binding of an agonist to a receptor can lead to a series of receptors activating. Agonists can operate together on a single receptor. Different agonists can bind to the same receptor but lead to different levels of activation.

Whether a Qi611S Protein induces expression or acts as an agonist of a particular protein can depend upon the context in which the protein is interacting, for example, the biological or metabolic pathways involved, the type(s) of cells involved (e.g., bacteria, cancer or immune cells), and/or phosphorylation or other ligand modification of the PPAR, ERK or GR.

Cancer Treatment

Because the PPAR receptor helps regulate normal cell differentiation and turnover and can therefore potentially regulate cancer cell hyperproliferation, this receptor has been shown to be a useful therapeutic target in malignant disease (Qian Gou, Xin Gong, Jianhua Jin, Juanjuan Shi, and Yongzhong Hou. Peroxisome proliferator-activated receptors (PPARs) are potential drug targets for cancer therapy. Oncotarget. 2017 Sep. 1; 8(36): 60704-60709). In this sense, it could be used as an adjuvant or as a sole therapeutic for various cancers.

In certain embodiments, the present invention provides compositions and methods for reducing, eliminating, suppressing, and/or preventing cancer cell proliferation. In some embodiments, the present invention can be combined with other methods of cancer treatment or cancer prevention, such as radiation therapy or chemotherapy.

As used herein, the term "cancer" refers to the presence of cells possessing abnormal growth characteristics, such as uncontrolled proliferation, immortality, metastatic potential, rapid growth and proliferation rate, perturbed oncogenic signaling, and certain characteristic morphological features. Cancer cells are typically, by definition, "malignant;" however, the present invention can also be useful in treatment of a benign tumor. Non-limiting examples of cancers include carcinomas, sarcomas, melanomas, lymphomas, and leukemia. In certain specific embodiments, cancers treatable according to the subject invention include cancers, such as solid tumors, of the breast, liver, GI tract (esophageal, gastric, intestinal/colon), skin, lung, pancreas and prostate. Also, hematopoietic cancers such as multiple myeloma and leukemias (acute promyelocytic leukemia adjuvant with arsenic-based chemotherapeutics) can be treated.

The cancer cell cycle can be halted at, for example, the mitotic phase, including prophase, prometaphase, metaphase, anaphase or any of the interphase stages including $G_1$, $S$, $G_2$, or $M$.

In an exemplary embodiment, induction and/or agonism of PPARγ can play a major role in the ubiquitous insulin-growth factor (IGF) system, which is involved in growth, development and metabolism, and cellular processes such as proliferation, survival, cell migration and differentiation. Modulation of the IGF system can be important for the treatment of cancer, which often takes over different aspects of the IGF system in order to enhance proliferation.

In the IGF system, in some cell contexts, PPARγ ligands reduce mitogen-activated protein kinase (MEK1/2) systems, which results in inhibition of ERK1/2-mediated PPARγ phosphorylation. In other contexts, PPARγ agonists can activate ERK1/2. Activated ERK1/2 can further lead to ERK-mediated PPARγ phosphorylation at Ser84/114. Phosphorylation of PPARγ can affect, for example, the expression of metabolic regulatory genes.

In certain embodiments, a Qi611S Protein can induce expression and/or activity of PPARγ, thus reducing MEK1/2 action and inhibiting ERK1/2-mediated phosphorylation of PPAR-γ. In certain embodiments, Qi611 S can bind or otherwise interact with PPARγ, e.g., as an agonist or ligand, leading to direct activation of ERK1/2 and phosphorylation of PPARγ.

In certain embodiments, the compositions can be useful for treating certain cancers due to the ability of Qi611S Proteins to enhance the expression and/or activity of PPARγ.

In certain breast cancers, PPARγ interacts with the hormone leptin, which is produced mainly by adipocytes, placenta and mammary epithelium and plays a significant role in the control of metabolism, reproductive processes, immune processes, angiogenesis, haemopoiesis and oxidation of lipids. Leptin enhances breast cancer cell proliferation by inhibiting pro-apoptosis signaling pathways and by favoring in vitro sensitivity to estrogens. Leptin may also promote mammary tumor growth through multiple mechanisms, including modulation of the extracellular environment, down-regulation of apoptosis and/or up-regulation of anti-apoptotic genes.

More specifically, PPARγ can counteract the function and expression of leptin in breast cancer. Leptin increases phosphorylation of GR through a cascade of kinase activations, and promotes pGR nuclear translocation. pGR stimulates the transcription of a leptin promoter by binding to a GU-rich element (GRE) motif. In the presence of a benzodiazepine receptor ligand (BRL), PPARγ binds to the GRE and forms a pGR/PPARγ complex, allowing for recruitment of nuclear co-receptors NCoR and SMRT, which inhibit leptin transcription and reduce breast tumor growth.

In certain embodiments, Qi611S Proteins can induce GR and/or pGR in certain cell systems. In certain embodiments, Qi611S Proteins can concurrently induce GR and PPAR expression, which can be useful for reducing tumor growth in cancer systems, such as, for example, the leptin-mediated growth of certain breast tumors. Thus, the compositions and methods of the present invention can be useful for treating, and/or preventing the spread of, cancer.

Anti-Inflammatory Activity and Immune Modulation

In some embodiments, a Qi611S Protein and/or cells comprising a nucleotide sequence encoding a Qi611S Protein can modulate the expression of skin innate immune peptides and/or cytokines involved in inflammation (e.g., PPARγ, interleukin-10 (IL-10), tumor necrosis factor alpha (TNFα), PERK, toll-like receptors (TLR), and/or filaggrin). Thus, in certain embodiments, the present compositions and methods can be used to enhance skin, and other, innate immune functions. Thus, in one embodiment the present compositions and methods can be used to improve the health and/or appearance of skin. In other embodiments, the compositions and methods can enhance skin barrier function by upregulating the expression of skin barrier proteins.

Because of the potential improved safety profile and the possibility of complete avoidance of glucocorticoid exposure, the application for a GR- and PPAR-activating compound is broad, and exists essentially anywhere GC are currently used. For instance, there is a need in respiratory disease to decrease inflammation without GC adverse effect or steroid tachyphylaxis, a condition in which GC induce internalization of the GR; however, activation of the glucocorticoid receptor (GR) during acute inflammation is important for lung function and survival during acute inflammation (Wepler M, Preuss J M, Merz T, Hartmann C, Wachter U, McCook O, Vogt J, Kress S, Grager M, Fink M, Scheuerle A, Maller P, Calzia E, Burret U, Radermacher P, Tuckermann J P, Vettorazzi S. Impaired Glucocorticoid Receptor Dimerization Aggravates LPS-Induced Circulatory and Pulmonary Dysfunction. Front Immunol. 2020 Jan. 23; 10:3152).

Advantageously, the compositions of the subject invention can be administered systemically or locally and can be used to reduce the dose of glucocorticoids required which mitigates side effects including immunosuppression.

Dermatologic Uses

Human skin comprises two compartments, the deep compartment (the dermis) and the surface compartment (the epidermis). The skin constitutes a barrier against external attacks, particularly chemical, mechanical, or infectious attacks, as well as a number of defensive reactions against environmental factors such as, for example, climate, ultraviolet rays, and tobacco, and/or xenobiotic factors, such as, for example, microorganisms. This property is referred to as the skin barrier function and is mainly provided by the outermost layer of the epidermis, namely the stratum corneum. Detrimental changes in the barrier can be reflected by, for example, cutaneous discomfort, sensory phenomena and/or cutaneous dryness.

There is also a need in the dermatologic field for a GR-activator that does not damage the tissue barrier. The use of GC results in damaged barrier function and decreased barrier protein production (Hatano Y, Elias P M, Crumrine D, Feingold K R, Katagiri K, Fujiwara S. Efficacy of combined peroxisome proliferator-activated receptor-α ligand and glucocorticoid therapy in a murine model of atopic dermatitis. J Invest Dermatol. 2011 September; 131 (9):1845-52). Therefore, unlike current GC topical treatments, a non-GC compound that can activate the GR can be used chronically, systemically and topically, including on areas of thin skin such as the face and hands. Furthermore, the angiotensin receptor can be activated by PPAR gamma ligands, of which this unique peptide may act. Many viruses use the angiotensin converting enzyme receptor (ACE-R) on cell surfaces as a means of entry. PPAR ligands, too, can directly act upon the angiotension conversting enzyme receptor directly or indirectly through the signaling pathway.

In certain embodiments, compositions and methods of the present invention are useful for preventing a reduction in the barrier function and/or to repair or regenerate barrier function by inducing or inhibiting, for example, PPARγ and/or pERK, which can modulate cell apoptosis, halting of the cell cycle, programmed cell death, and/or cancer cell invasion of tissues in certain cell systems.

Disorders associated with disruption of the skin and/or mucosal barrier (e.g., face, body, and scalp) include, but are not limited to, psoriasis, icthyosis, sarcoidosis, atherosclerosis, inflammatory bowel disease, acne (including hidradenitis suppurativa), burns, diaper rash, Netherton's syndrome, actinic keratosis, dermatomycoses, dermatosis or ectodermal dysplasia, atopic dermatitis, contact dermatitis, seborrheic dermatitis, vulgaris, eosinophilic esophagitis, filaggrin deficiency, and other disorders associated with damage or breakdown of the skin and/or mucosal barrier.

In some embodiments, repair or regeneration of the barrier includes repair or regeneration of a mucous membrane. Mucous membranes include mucosa of the mouth (including mucosa of the cheek, the soft palate, the tongue, including the under surface of the tongue and the floor of the mouth), the nose, the throat (including mucosa of the pharynx, the larynx, the trachea and the esophagus), the bronchi, the lungs, the eye, the ear, the gastrointestinal tract, the vagina, the penis, the urethra, the bladder, and the anus.

In one embodiment, the compositions of the subject invention can be used to treat dry skin, including dry facial skin. The compositions can be formulated as leave-on, rinse-off and/or mists (including facial mists).

The active agent, e.g., a Qi611S Protein can be present at 0.01% to 2%, or any range therebetween, including, for example, 0.1 to 0.5%.

Maternal-Fetal Medicine

The compositions and methods of the subject invention can be used to improve maternal-fetal health, including in the treatment of:
Pre-eclampsia;
Maternal diabetes;
Eclampsia;
Low birth weight;
Normal pregnancy;
Intrauterine growth retardation (IUGR);
Necrotizing enterocolitis; and
Pre-term labor.

Neurologic Conditions

The compositions and methods of the subject invention can be used to improve neurologic conditions, including in the treatment of:
Cognitive performance enhancement;
Alzheimer's disease;
Parkinson's disease;
Neurologic regeneration; and
Multiple sclerosis.

Cardiovascular Conditions

The compositions and methods of the subject invention can be used to improve cardiovascular conditions, including in the treatment of:
Coronary artery disease;
Systemic delivery and intrastent delivery as medical device;
Acute cerebrovascular event; and
Systemic delivery and intrastent delivery as medical device+/−TPA.

Progressive Fibrotic Conditions

Preclinical studies have implicated the PPAR receptor as a drug target for antifibrotic therapy (McVicker B L, Bennett R G. Novel Anti-fibrotic Therapies. Front Pharmacol. 2017 May 31; 8:318). Therapies can be systemic, inhaled or otherwise topically administered, or delivered via in-stent medical device. Conditions that can be addressed include:
Cardiovascular (cardiac remodeling);
Renal (renal sclerosis);
Nasal (nasal polyposis);
Pulmonary (pulmonary interstitial fibrosis, chronic asthma with airway remodeling);
Liver (primary biliary cirrhosis, primary sclerosing cholangitis, non-alcoholic steatohepatitis);
Gastrointestinal (inflammatory bowel disease-related fibrosis); and
Rheumatologic (systemic sclerosis).

Gastrointestinal Inflammatory Conditions Inflammatory bowel diseases (e.g., ulcerative colitis and Crohn's disease) can also be treated using the compositions and methods of the subject invention.

Treatment of Infections

In certain embodiments, the compositions and methods of the present invention can also be used in the treatment of acute and chronic infections. Infections occur where disease-causing microorganisms invade the tissues of the body. Those microorganisms and the toxins that they produce react with the tissues of the body, often causing immune reactions by the infected host. Infections may be caused by bacteria, viruses, viroids, fungi and other parasites. Infections may occur via any of the tissues of the body, such as the skin, gut or membranes.

In one embodiment, the Qi611S Proteins can be used in various formulations as a means by which to reduce viral load inoculum and competitive antagonism acting through the ACE-R whether as a prophylactic or primary treatment for said viral infections.

Viral infections can include, for example, influenza, coronavirus, chronic Epstein-Barr virus, cytomegalovirus and other herpes-type virus infection, which are ubiquitous in the population and are associated with a decrease on the immune surveillance. Some viral infections can lead to cancer. For example, Epstein-Barr virus infection can be a risk factor of Hodgkin's lymphoma, a cancer of lymphocytes.

Prevention and treatment of acute and chronic pulmonary sequelae associated with viral respiratory infections, including COVID-19.

The compositions and methods can also be used for the prevention and treatment of glucocorticoid resistance in asthma and COPD.

In specific embodiments, the present invention provides compositions and methods for the treatment and/or prevention of infection of the external surface of the body, and particularly of the skin. The proteins, compositions and cells provided herein may be applied separately, sequentially or simultaneously with exposure to the infective agent.

In certain embodiments, the infection may be caused by a bacterium, such as pathogenic *Staphylococcus aureus* bacteria. *S. aureus* is a transient colonizer of skin predominantly in the moist, warm regions of the body such as the groin, axilla and the anterior nares. Up to 60% of the world's populations are intermittent carriers while another 20% may be stably colonized. While normal carriage is asymptomatic, *S. aureus* may invade tissues (e.g., through broken skin) where it causes diseases ranging from the relatively minor impetigo and scalded skin syndrome, to life threatening conditions such as septicemia. Furthermore, *S. aureus* infection is often a secondary phenomenon in skin with underlying conditions such as atopic dermatitis (AD).

In certain embodiments, the compositions of the present invention are useful for the treatment of infections by a number of pathogenic bacteria including, but not limited to, *Staphylococcus* spp. (*Staphylococcus saprophyticus, Staphylococcus xylosus, Staphylococcus lugdunensis, Staphylococcus schleiferi, Staphylococcus caprae, Staphylococcus saprophyticus, Staphylococcus hominis, Staphylococcus aureus*), *Pseudomonas* spp., *Enterococcus faecalis*, vancomycin-resistant *Enterococcus* (VRE), *Bacillus cereus, Bacillus subtilis, Listeria monocytogenes, Streptococcus pyrogenes, Streptococcus salivariu, Streptococcus mutans*, and *Streptococcus pneumonia*. Other pathogenic bacteria will be readily recognized by a person skilled in the art.

In some embodiments, compositions comprising a Qi611S Protein and/or a cell capable of producing a Qi611S Protein, have the advantage of promoting the growth of commensal bacteria in the human skin microbiome. Non-limiting examples of the commensal bacteria include, but are not limited to, *Staphylococcus epidermidis, Staphylococcus warneri, Streptococcus mitis, Propionibacterium acnes, Corynebacterium* spp., and *Acinetobacter johnsonii.*

Ophthalmologic Uses

There is a need in the ophthalmic field for a non-GC GR-activator that does not damage ocular tissue, increase ophthalmic pressures, or predispose to glaucoma or cataract formation. These are all known complications of GC use. A non-GC GR-activator in combination with PPAR activation would be of particular use in the topical and intraocular treatment of ocular inflammation and ocular disease. PPAR signaling is an important activation pathway for the genesis and maintenance of several ocular tissue types including meibomian glands, conjunctival goblets cells, corneal limbal stem cells, trabecular meshwork, uveal tissue and choroidal membranes. Furthermore, the angiotensin receptor can be activated by PPAR gamma ligands, of which this unique peptide may act.

Accordingly, the Qi611 S Proteins of the subject invention can, advantageously, be used in the prevention and/or treatment of:
- diabetic retinopathy (DR);
- choroidal neovascularization (CNV);
- glaucoma;
- corneal neovascularization;
- diabetic macular edema;
- age-related macular degeneration (ARMD);
- diabetic neovascularization;
- keratitis;
- corneal limbal stem cell failure;
- optic neuropathy;
- dry eye disease;
- Meibomian gland dysfunction; and
- Allergic conjunctivitis.

Treatment of Surfaces

In certain embodiments, the present compositions can be utilized as an antimicrobial cleaning product or surface coating, which is not for medical treatment of the human or animal body. Thus, in specific embodiments, the compositions can be used to disinfect inanimate surfaces.

Administration to a Subject

The present invention provides methods of providing a therapeutic and/or cosmetic benefit to a subject in need thereof, where a therapeutically-effective or cosmetically-effective amount of a composition comprising a Qi611 S Protein and/or a cell capable of producing a Qi611 S Protein, is administered to a subject in need thereof. In some embodiments, the composition can comprise, and/or be administered concurrently with, a pharmaceutically- or cosmetically-acceptable carrier.

In one embodiment, the method is used to treat a dermatological disorder, and/or to enhance the health and/or appearance of skin. In one embodiment, the method is used to control a bacterial, fungal or viral infection or contaminant in or on the body, or on an inanimate surface. In one embodiment, the method is used to treat, and/or prevent the spread of, cancer. In one embodiment, the method is used to treat inflammation and/or metabolic dysfunction.

The composition may be administered alone or in combination with other treatments, either simultaneously or sequentially dependent upon the condition to be treated. The compositions provided herein may be dissolved in, suspended in, or admixed with one or more other active or inert ingredients. In certain embodiments, the composition can be formulated as a food item, capsule, pill, drinkable liquid, lotion, cream, emulsion, ointment, oil, gel, serum, mist, vapor, and/or combinations thereof. The compositions may also be presented in a liposome or other microparticle.

The compositions provided herein may also include other pharmaceutically-acceptable and/or cosmetically-acceptable ingredients known to those skilled in the art, including, but not limited to, carriers, adjuvants, excipients, diluents, fillers, buffers, preservatives, anti-oxidants, lubricants, stabilizers, solubilizers, surfactants (e.g., wetting agents), masking agents, coloring agents and others as described below.

The formulations may further comprise other active agents including, for example, other therapeutic or prophylactic agents.

As provided herein, "pharmaceutically-acceptable" refers to approved or approvable by a regulatory agency of the US Federal Government or a state government or listed in the U.S. Pharmacopeia or other generally recognized pharmacopeia for use in animals, including humans.

As used herein, "cosmetically-acceptable," "dermatologically-acceptable," and "topically-acceptable" are used interchangeably and are intended to mean that a particular component is safe and non-toxic for application to the integument (e.g., skin) at the levels employed. In one embodiment, the components of the composition are recognized as being Generally Regarded as Safe (GRAS).

"Pharmaceutically-acceptable" and "cosmetically-acceptable" carriers or adjuvants are those that can be administered to a subject, together with an active ingredient, that do not destroy the pharmacological or cosmetic activity, respectively, thereof, and which are nontoxic when administered in doses sufficient to deliver a therapeutic or cosmetic amount of the compositions provided herein. As used herein, "carrier" includes excipients.

Carriers and/or adjuvants can comprise substances used for administrating the composition according to specific routes, including, for example, oral administration, injection (e.g., subcutaneous, intravenous, intramuscular, intraperitoneal, intrathecal, and/or subdermal), and/or topical administration (e.g., via dermal absorption).

Carriers, according the subject invention, can include any and all solvents, diluents, buffers (such as neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilizers (e.g., Polysorbate 65, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners (e.g. carbomer, gelatin, or sodium alginate), coatings, preservatives (e.g., Thimerosal, benzyl alcohol, polyquaterium), antioxidants (e.g., ascorbic acid, sodium metabisulfite), tonicity controlling agents, absorption delaying agents, adjuvants, bulking agents (e.g., lactose, mannitol), and the like. The use of carriers and/or excipients in the field of drugs, cosmetics and supplements is well known.

In one embodiment, the method is used to treat a dermatological disorder, and/or to enhance the health and/or appearance of skin.

In preferred embodiments, the compositions are formulated for topical administration, particularly for use or application to, or on, the skin. As used herein, "topical" means suitable for local application externally to the skin, or cutaneous application. In other words, a topical composition is not intended for application to a subject via oral, intravenous, intramuscular, intrathecal, subcutaneous, sublingual, buccal, rectal, vaginal, inhalation, ocular or otic routes.

Such formulations may be useful for removing, killing, or preventing the adhesion and accumulation of pathogenic bacteria, such as MRSA, on a biological or non-biotic surface, or inhibiting the action or growth of infectious bacteria.

Formulations suitable for topical, dermal and/or transdermal administration include, but are not limited to, gels, pastes, ointments, creams, lotions, oils, patches, adhesive plasters, bandages, dressings, depots, cements, glues, reservoirs, rinses, sprays, drops, foams, powders, sponges, tapes, vapors, tincture, and transdermal patches.

Ointments are typically prepared from the cosmetic compositions provided herein and a paraffinic or a water-miscible ointment base.

Creams are typically prepared from the cosmetic compositions provided herein and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol, polyethylene glycol, and mixtures thereof. As would be readily appreciated by one skilled in the art, formulations according to the subject invention could also comprise other alcohols, such as, for example, isopropyl alcohol or ethanol, and could also cover other alcohol based formulations, for example alcohol-based hand sanitizers.

The topical formulations may include a compound that enhances absorption or penetration of the active compound through the skin or other affected areas. Examples of such dermal penetration enhancers include dimethylsulfoxide and related analogs.

Emulsions are typically prepared from the cosmetic compositions provided herein and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabilizer. It is also preferred to include both oil and a fat. Together, the emulsifier(s), with or without stabilizer(s), make up the so-called emulsifying wax, and the wax together with the oil and/or fat make up the so-called emulsifying ointment base, which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Additional topical components can include, for example, emollients, such as carnauba wax, cetyl alcohol, cetyl ester wax, emulsifying wax, hydrous lanolin, lanolin, lanolin alcohols, microcrystalline wax, paraffin, petrolatum, polyethylene glycol, stearic acid, stearyl alcohol, white beeswax, or yellow beeswax. Additionally, the compositions may contain humectants, such as glycerin, propylene glycol, polyethylene glycol, sorbitol solution, and 1,2,6 hexanetriol or permeation enhancers, such as ethanol, isopropyl alcohol, or oleic acid.

In one embodiment, the method is used to control an bacterial, fungal or viral infection or contaminant in, or on, the body, or on an inanimate surface.

In specific embodiments, the composition can be used as an antibacterial composition for treating biomaterials, implants, catheters, prostheses (including stents, valves, eyes, hearing aids, gastric bands, dentures, and artificial joint replacements), surgical instruments or other medical devices prior to administration to, or treatment of, or use with, a subject.

The antibacterial compositions may be useful for treating surfaces prone to colonization or exposure to bacteria, such as handrails, food preparation surfaces, kitchen surfaces or equipment, tables, sinks, toilets or other bathroom hardware.

Antibacterial compositions may comprise agents in addition to a Qi611 S Protein and/or cells capable of producing a Qi611S Protein, such as cleaning agents, stabilizers, anionic surfactants, perfumes, chelating agents, acids, alkalis, buffers or detergents. Such agents may facilitate or enhance the antibacterial properties of the compositions, such as killing or inhibiting bacteria, or preventing the recolonization of the cleaned surface.

In some embodiments, the compositions are formulated for administration via other non-topical routes, such as, for example, via oral, intravenous, intramuscular, intrathecal, subcutaneous, sublingual, buccal, rectal, vaginal, inhalation, ocular and/or otic routes. Administration can be systemic and/or it can be local, for example, at the site of an infection or a tumor in a subject's body.

In one embodiment, the subject composition is formulated as an orally-consumable product, such as a food item, capsule, pill, or drinkable liquid. An orally deliverable health-promoting compound is any physiologically active substance delivered via initial absorption in the gastrointestinal tract or into the mucus membranes of the mouth.

The composition can also be formulated to be administered via, for example, injection, which includes intravenously, intraperitoneally, intramuscularly, intrathecally, or subcutaneously. The compositions can also be administered sublingually, buccally, rectally, or vaginally. Furthermore, the compositions can be sprayed into the nose for absorption through the nasal membrane, nebulized, inhaled via the mouth or nose, or administered in the eye or ear.

Formulations can include, for example, orally-consumable products, emulsions, tablets, capsules, powders, foams, granules, solutions, swabs, drops, suspensions, suppositories, injections, inhalants, and aerosols.

Orally-consumable products, according to the invention, are any preparations or compositions suitable for consumption, for nutrition, for oral hygiene, or for pleasure and are products intended to be introduced into the human or animal oral cavity, to remain there for a certain period of time, and then either to be swallowed (e.g., food ready for consumption or pills) or to be removed from the oral cavity again (e.g., chewing gums or products of oral hygiene or medical mouth washes).

Orally consumable products include all substances or products intended to be ingested by humans or animals in a processed, semi-processed, or unprocessed state. This also includes substances that are added to orally consumable products (particularly food and pharmaceutical products) during their production, treatment, or processing and intended to be introduced into the human or animal oral cavity.

Orally consumable products can also include substances intended to be swallowed by humans or animals and then digested in an unmodified, prepared, or processed state. The orally-consumable products, according to the invention, also include casings, coatings, or other encapsulations that are intended to be swallowed together with the product or for which swallowing is to be anticipated.

In one embodiment, the orally consumable product is a capsule, pill, syrup, emulsion, or liquid suspension containing a desired orally deliverable substance (e.g., a Qi611 S Protein). In one embodiment, the orally consumable product can comprise an orally deliverable substance in powder form, which can be mixed with water or another liquid to produce a drinkable orally consumable product.

In some embodiments, the orally-consumable product, according to the invention, can comprise one or more formulations intended for nutrition or pleasure. These include baking products (e.g., bread, dry biscuits, cake, and other pastries), sweets (e.g., chocolates, chocolate bar products, other bar products, fruit gum, coated tablets, hard caramels, toffees and caramels, and chewing gum), alcoholic or non-alcoholic beverages (e.g., cocoa, coffee, green tea, black tea, black or green tea beverages enriched with extracts of green or black tea, Rooibos tea, other herbal teas, fruit-containing lemonades, isotonic beverages, soft drinks, nectars, fruit and vegetable juices, and fruit or vegetable juice preparations), instant beverages (e.g., instant cocoa beverages, instant tea beverages, and instant coffee beverages), meat products (e.g., ham, fresh or raw sausage preparations, and seasoned or marinated fresh meat or salted meat products), eggs or egg products (e.g., dried whole egg, egg white, and egg yolk), cereal products (e.g., breakfast cereals, muesli bars, and pre-cooked instant rice products), dairy products (e.g., whole fat or fat reduced or fat-free milk beverages, rice pudding, yoghurt, kefir, cream cheese, soft cheese, hard cheese, dried milk powder, whey, butter, buttermilk, and partly or wholly hydrolyzed products containing milk proteins), products from soy protein or other soy bean fractions (e.g., soy milk and products prepared thereof, beverages containing isolated or enzymatically treated soy protein, soy flour containing beverages, preparations containing soy lecithin, fermented products, such as tofu or tempeh products prepared thereof and mixtures with fruit preparations and, optionally, flavoring substances), fruit preparations (e.g., jams, fruit ice cream, fruit sauces, and fruit fillings), vegetable preparations (e.g., ketchup, sauces, dried vegetables, deep-freeze vegetables, pre-cooked vegetables, and boiled vegetables), snack articles (e.g., baked or fried potato chips (crisps) or potato dough products and extrudates on the basis of maize or peanuts), products on the basis of fat and oil or emulsions thereof (e.g., mayonnaise, remoulade, and dressings), other ready-made meals and soups (e.g., dry soups, instant soups, and pre-cooked soups), seasonings (e.g., sprinkle-on seasonings), sweetener compositions (e.g., tablets, sachets, and other preparations for sweetening or whitening beverages or other food). The present compositions may also serve as semi-finished products for the production of other compositions intended for nutrition or pleasure.

In one embodiment, the composition can be made into aerosol formulations so that, for example, it can be nebulized or inhaled. Suitable pharmaceutical formulations for administration in the form of aerosols or sprays are, for example, solutions, suspensions, or emulsions. Formulations for oral or nasal aerosol or inhalation administration may also be formulated with illustrative carriers, including, for example, saline, polyethylene glycol or glycols, DPPC, methylcellulose, or in mixture with powdered dispersing agents or fluorocarbons. Aerosol formulations can be placed into pressurized propellants, such as dichlorodifluoromethane, propane, nitrogen, fluorocarbons, and/or other solubilizing or dispersing agents known in the art. Illustratively, delivery may be by use of a single-use delivery device, a mist nebulizer, a breath-activated powder inhaler, an aerosol metered-dose inhaler (MDI), or any other of the numerous nebulizer delivery devices available in the art. Additionally, mist tents or direct administration through endotracheal tubes may also be used.

In one embodiment, the composition can be formulated for administration via injection, for example, as a solution or suspension. The solution or suspension can comprise suitable non-toxic, parenterally-acceptable diluents or solvents, such as mannitol, 1,3-butanediol, water, Ringer's solution, or isotonic sodium chloride solution, or suitable dispersing or wetting and suspending agents, such as sterile, non-irritant, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600, and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance is an acceptable isotonic solution, such as 5% dextrose or 0.9% sodium chloride; or 0.01-0.2% dipalmitoyl diphosphatidyleholine in USP WFI and 1 to 10% squalene or parenteral vegetable oil-in-water emulsions.

Additional formulations envisioned for administration to a subject include ear drops and eye drops, for treating, e.g., infections of the ears and/or eyes, and/or dry eye.

For ophthalmic use, exemplary formulations are as follows:

Isotonic Sodium Chloride Solution:
    Sodium Chloride 0.9%
    Benzalkonium chloride 1:100,000
    sterile water Buffer Solution
    boric acid 1.9%
    Benzalkonium chloride 1:100,000
    Sodium sulfite, anhydrous 0.1%
    Phenylmercuric nitrate 1:50,000

Artificial Tear Solution:
    Polyvinyl alcohol 1.5%
    povidone 0.5%
    Chlorobutanol 0.5%
    Ethylenediamintetaacetic acid 0.01%
    Disodium edetate 0.05%
    white petrolatum 55%
    mineral oil 41%
    lanolin 2%
    thimerosal 0.002%
    ammonium acetate 0.0077%
    Human albumin 0.1%
    Vehicles: average drop is 25 to 50 microliters Further components can be added to the compositions described herein as determined by the skilled artisan, for example, buffers, carriers, viscosity modifiers, preservatives, flavorings, dyes, and other ingredients specific for an intended use. One skilled in this art will recognize that the above description is illustrative rather than exhaustive. Indeed, many additional formulations techniques and pharmaceutically- and/or cosmetically-acceptable excipients and carrier solutions suitable for particular modes of administration are well-known to those skilled in the art.

All patents, patent applications, provisional applications, and publications referred to or cited herein are incorporated by reference in their entirety, including all figures and tables, to the extent they are not inconsistent with the explicit teachings of this specification.

EXAMPLES

It should be understood that the examples and embodiments described herein are for illustrative purposes only and that various modifications or changes in light thereof will be suggested to persons skilled in the art and are to be included within the spirit and purview of this application.

Example 1—Isolation and Transformation of Qi611S Gene into *E. coli* BL21

A gene encoding Qi611S, Qi611S, can be isolated from *Lactobacillus fermentum* Qi6 and transformed into *E. coli* BL21. As shown in FIG. 3, *E. coli* BL21 is capable of synthesizing a Qi611S protein.

Primers that were used to amplify Qi611S from LF Qi6 can be used to confirm the presence of Qi611S in the *E. coli* cell. The primers used for cloning of Qi611S into the pET-15b vector are listed in Table 2 (see also FIGS. 1-2). These specially-designed primers were obtained from Integrated DNA Technologies (IDT) (Coralville, Iowa).

TABLE 2

| Primers used in the cloning of Qi611S for transformation into *E. coli* BL21. | |
|---|---|
| Primer Name | Primer Sequence (5'-3') |
| Lacto F | CATATGGATAACCGGATTTTCTTCA (SEQ ID NO: 3) |
| Lacto R | GGATCCTTAGAGGTTTTTCTTAATC (SEQ ID NO: 4) |

DNA was isolated and amplified from the Lf Qi6 chromosome that encodes Qi611S using the primers featured in Table 2. The primers enabled the use of two restriction enzymes, NdeI and BamHI, for a restriction enzyme digest of the amplified Qi611S gene and the multiple cloning site of the pET-15b vector.

Once the amplified DNA and the vector are digested using the restriction enzymes, the Qi611S gene is ligated into the vector. The vector can then be transformed into *E. coli* BL21.

The transformed *E. coli* culture is grown overnight at 37° C. and individual colonies are tested for the presence of Qi611S using PCR. Once positive clones are identified, the bacteria can then be grown to identify if Qi611S is successfully encoding synthesis of Qi611S.

The Qi611S protein can be detected by silver staining on SDS-PAGE gel. The SDS-PAGE gel is loaded with released protein samples from *E. coli* BL21 that is expressing Qi611 S. The pET-15b vector encodes a polyhistidine-tag, enabling the identification of a synthesized protein without having an antibody specific to the Qi611S. Additionally, the pET-15b encodes the thrombin protease cleavage site (Leu-Val-Pro-Arg-Gly-Ser) to enable removal of the polyhistidine-tag.

Example 2—Qi611 S Induces PPARγ in Skin

Ex vivo skin cultures were treated with chosen concentrations of Qi611S (0.1% or 0.5%) or dexamethasone (10 mM), inoculated with 100 µl of MRSA cultures, and grown overnight. Skin tissues were then homogenized, released proteins were separated using electrophoresis, and a western blot was used to determine the amount of PPARγ in each sample. β-actin was used as a reference protein. Skin cells expressed more PPARγ in the presence of MRSA and Qi611 S (FIGS. 4A-4B).

Ex vivo skin cultures were also treated with chosen concentrations of Qi611 S (0, 0.125, 0.25, 0.5, 1.0, and 2.0%) and grown overnight. Skin tissues were then homogenized, released proteins were separated using electrophoresis, and a western blot was used to determine the amount of PPARγ in each sample. β-actin was used as a reference protein. Skin cells expressed, in general, more PPARγ as the concentration of Qi611S increased (FIGS. 5A-5B).

Example 3—Qi611S Induces Perk (Phosphorylated ERK1/2) in Skin

Ex vivo skin cultures were treated with chosen concentrations of Qi611S (0.1% or 0.5%) or dexamethasone (10 mM), inoculated with 100 µl of MRSA cultures, and grown overnight. Skin tissues were then homogenized, released proteins were separated using electrophoresis, and a western blot was used to determine the amount of pERK in each sample. β-actin is used as a reference protein. Skin cells expressed more pERK in the presence of MRSA and Qi611S (FIGS. 6A-6B).

Ex vivo skin cultures were also treated with chosen concentrations of Qi611S (0, 0.125, 0.25, 0.5, 1.0, and 2.0%) and grown overnight. Skin tissues were then homogenized, released proteins were separated using electrophoresis, and a western blot was used to determine the amount of pERK in each sample. β-actin was used as a reference protein. Skin cells expressed the greatest pERK at 0.25% Qi611 S (FIGS. 7A-7B).

Example 4—Qi611S Induces pGR in Skin

Ex vivo skin cultures were treated with chosen concentrations of Qi611S (1%, 2%, or 5%), inoculated with 100 µl of MRSA cultures, and grown overnight. Skin tissues were then homogenized, released proteins were separated using electrophoresis, and a western blot was used to determine the amount of pGR in each sample. β-actin is used as a reference protein. As shown in FIGS. 8A-8B, skin cells expressed more pGR in the presence of Qi611 S.

Example 5—Qi611S Induces Gr Gene Expression in Zebra Fish

RT-qPCR was used to measure the expression level of the gene that encodes GR in zebra fish cells when treated with increasing concentrations of Qi611 S (0, 1, 2, and 5% (W/V)). Tissue explants for qPCR were flash frozen in liquid nitrogen. Total RNA was isolated and purified. mRNA was isolated and reverse transcribed, and the resulting cDNA was identified and quantified. The mRNA expression levels were normalized to the β-microglobulin reference gene.

The results indicate that the presence of Qi611S induces increased expression of the gene encoding GR in zebra fish (FIG. 9).

Example 6—Qi611 S Induces pGR in Caco2 Cells

CaCo-2 cells are a line of human epithelial colorectal adenocarcinoma cells. CaCo-2 cultures were treated with chosen concentrations of Qi611S (0.125%, 0.25%, 0.5%, 1%, and 2%) and grown overnight. CaCo-2 cultures were then homogenized and a western blot was used to determine the amount of pGR in each sample. β-actin is used as a reference protein. As shown in FIGS. 10A-10B, Qi611 S induces pGR expression in CaCO-2 cells.

Example 7—Qi611S Inhibits MRSA Biofilm Formation

To assess the inhibition of the MRSA biofilm, MRSA was added to the wells of sterile polystyrene, tissue-culture plates. Growth control wells received equal parts MRSA and culture medium. Chosen concentrations of Qi611 S (1.56, 3.12, 6.25, 12.5, 25, 50, and 100 ng/µL) or the negative control (0 ng/µL of Qi611S) were added. The plate was incubated at 37° C. for 18 h and then biofilm quantified by crystal violet staining. The degree of anti-biofilm efficacy was represented by direct visualization and measurement of bacterial growth in individual treated wells, wherein the smaller the diameter of growth, the greater the anti-biofilm efficacy of that particular compound. Each plate was read at 590 nm and 600 nm using a spectrophotometer (SpectraMax Plus384, Molecular Devices, Sunnyvale, CA). Qi611S was able to significantly inhibit biofilm formation of MRSA (FIG. 11).

REFERENCES

1. Subhadra B, Krier J, Hofstee K et al. Draft whole-genome sequence of *Lactobacillus fermentum* LfQi6, derived from the human microbiome. Genome Announc 2015: 3(3): e00423-15. doi:10.1128/genomeA.00423-15.
2. Posno M, Leer R J, van Luijk et al. Incompatibility of *Lactobacillus* Vectors with Replicons Derived from Small Cryptic *Lactobacillus* Plasmids and Segregational Instability of the Introduced Vectors. Applied and Environmental Microbiology 1991: 57(6): 1822-1828.
3. Felten A, Grandry B, Lagrange P H et al. Evaluation of Three Techniques for Detection of Low-Level Methicillin-Resistant *Staphylococcus aureus* (MRSA): a Disk Diffusion Method with Cefoxitin and Moxalactam, the Vitek 2 System, and the MRSA-Screen Latex Agglutination Test. J Clin Microbiol 2002: 40 (8): 2766-2771.

We claim:

1. A method for treating dry eye disease or Meibomian gland dysfunction, wherein said method comprises administering, to a subject in need of such treatment, a therapeutically-effective amount of an isolated protein, or a cell expressing said protein, wherein the protein comprises SEQ ID NO: 1.

2. The method of claim 1, used to treat dry eye disease.

3. The method of claim 1, wherein the protein consists of SEQ ID NO: 1.

4. The method of claim 1, used to treat Meibomian gland dysfunction.

* * * * *

UNITED STATES PATENT AND TRADEMARK OFFICE
CERTIFICATE OF CORRECTION

| | | |
|---|---|---|
| PATENT NO. | : 12,195,502 B2 | Page 1 of 1 |
| APPLICATION NO. | : 17/312484 | |
| DATED | : January 14, 2025 | |
| INVENTOR(S) | : Nicholas T. Monsul et al. | |

It is certified that error appears in the above-identified patent and that said Letters Patent is hereby corrected as shown below:

In the Specification

<u>Column 4,</u>
Line 13, "Downregulates 110-Hydroxysteroid" should read -- Downregulates 11β-Hydroxysteroid --.

<u>Column 8,</u>
Line 20, ""Qi61 S" refers to" should read -- "Qi611S" refers to --.

<u>Column 12,</u>
Line 43, "Qi61 S Proteins," should read -- Qi611S Proteins, --.

<u>Column 33,</u>
Line 1, "Caco2 Cells" should read -- CaCo2 Cells --.

Signed and Sealed this
Tenth Day of June, 2025

Coke Morgan Stewart
*Acting Director of the United States Patent and Trademark Office*

SEQUENCE LISTING

```
<160> NUMBER OF SEQ ID NOS: 6

<210> SEQ ID NO 1
<211> LENGTH: 74
<212> TYPE: PRT
<213> ORGANISM: Lactobacillus fermentum

<400> SEQUENCE: 1

Met Asp Asn Arg Ile Phe Phe Asn Pro Gly Asp Ser Ile Ala Asn Ile
1               5                  10                  15

His Asp Tyr Asn Glu Ala Val Arg Lys Gly Gln Ile Phe Lys Lys Glu
            20                  25                  30

Gln Gln Ala Gly Asp Leu Val Ile Ala Lys Gly Pro Asp Asp Glu Glu
        35                  40                  45

Tyr Ala Ile Phe Tyr Ala Asn Asp Ala Leu Pro Ala Asp His Glu Gln
    50                  55                  60

Ser Gln Pro Tyr Glu Ile Lys Lys Asn Leu
65                  70

<210> SEQ ID NO 2
<211> LENGTH: 225
<212> TYPE: DNA
<213> ORGANISM: Lactobacillus fermentum

<400> SEQUENCE: 2
atggataacc ggattttctt caaccccggc gactcgatcg ccaacatcca cgactacaac      60
gaagccgtcc gcaagggcca aatcttcaaa aaggaacagc aggccggcga cctcgtgatc     120
gctaagggtc ccgatgacga agaatacgcc atcttctacg ccaacgatgc cctgcccgcc     180
gaccacgagc aatcccaacc ctacgagatt aagaaaaacc tctaa                     225

<210> SEQ ID NO 3
<211> LENGTH: 25
<212> TYPE: DNA
<213> ORGANISM: Lactobacillus fermentum

<400> SEQUENCE: 3
```

```
catatggata accggatttt cttca                                          25

<210> SEQ ID NO 4
<211> LENGTH: 25
<212> TYPE: DNA
<213> ORGANISM: Lactobacillus fermentum

<400> SEQUENCE: 4
ggatccttag aggtttttct taatc                                          25

<210> SEQ ID NO 5
<211> LENGTH: 287
<212> TYPE: DNA
<213> ORGANISM: Artificial sequence
<220> FEATURE:
<223> OTHER INFORMATION: primer

<400> SEQUENCE: 5
agatctcgat cccgcgaaat taatacgact cactataggg gaattgtgag cggataacaa    60
ttcccctcta gaaataattt tgtttaactt taagaaggag atataccatg gcagcagcc    120 atcatcatca tcatcacagc agcggcctgg tgccgcgcgg cagccatatg ctcgaggatc   180
cggctgctaa caaagcccga aggaagctg agttggctgc tgccaccgct gagcaataac    240
tagcataacc ccttggggcc tctaaacggg tcttgagggg tttttg                  287

<210> SEQ ID NO 6
<211> LENGTH: 43
<212> TYPE: PRT
<213> ORGANISM: Artificial sequence
<220> FEATURE:
<223> OTHER INFORMATION: primer

<400> SEQUENCE: 6

Met Gly Ser Ser His His His His His His Ser Ser Gly Leu Val Pro
1               5                   10                  15

Arg Gly Ser His Met Leu Glu Asp Pro Ala Ala Asn Lys Ala Arg Lys
            20                  25                  30

Glu Ala Glu Leu Ala Ala Ala Thr Ala Glu Gln
            35                  40
```